United States Patent
Whitehurst et al.

(10) Patent No.: US 7,203,548 B2
(45) Date of Patent: Apr. 10, 2007

(54) CAVERNOUS NERVE STIMULATION VIA UNIDIRECTIONAL PROPAGATION OF ACTION POTENTIALS

(75) Inventors: Todd K Whitehurst, Santa Clarita, CA (US); James P McGivern, Stevenson Ranch, CA (US); Rafael Carbunaru, Sherman Oaks, CA (US); Matthew I Haller, Valley Village, CA (US); Tom Xiaohai He, Simi Valley, CA (US); Kerry Bradley, Glendale, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 463 days.

(21) Appl. No.: 10/176,743

(22) Filed: Jun. 20, 2002

(65) Prior Publication Data

US 2003/0236557 A1 Dec. 25, 2003

(51) Int. Cl.
*A61N 1/05* (2006.01)
*A61N 1/18* (2006.01)

(52) U.S. Cl. .......................... 607/39; 607/48; 607/118
(58) Field of Classification Search .............. 607/39, 607/45, 48, 118
See application file for complete search history.

(56) References Cited

U.S. PATENT DOCUMENTS

| | | |
|---|---|---|
| 3,850,161 A | 11/1974 | Liss |
| 3,881,495 A | 5/1975 | Pannozzo et al. |
| 3,941,136 A | 3/1976 | Bucalo ........................ 607/39 |
| 4,232,679 A | 11/1980 | Schulman |
| 4,408,608 A * | 10/1983 | Daly et al. .................... 607/57 |
| 4,467,809 A | 8/1984 | Brighton ...................... 607/51 |
| 4,481,950 A | 11/1984 | Duggan |
| 4,542,753 A | 9/1985 | Brenman et al. ............. 607/39 |
| 4,585,005 A | 4/1986 | Lue et al. ..................... 607/39 |
| 4,590,946 A | 5/1986 | Loeb .......................... 600/315 |
| 4,602,624 A | 7/1986 | Naples et al. ............... 607/118 |
| 4,608,985 A * | 9/1986 | Crish et al. ................... 607/74 |
| 4,628,942 A | 12/1986 | Sweeney et al. ............ 607/118 |

(Continued)

FOREIGN PATENT DOCUMENTS

WO WO-98/37926 A1 9/1998

(Continued)

OTHER PUBLICATIONS

Barker, et al., "Determination of the Distribution of Conduction Velocities in Human Nerve Trunks", Biomedical Engineering, vol. 26(2), (1979), pp. 76-81.

(Continued)

*Primary Examiner*—Robert E. Pezzuto
*Assistant Examiner*—Tammie K. Heller
(74) *Attorney, Agent, or Firm*—Fish & Richardson P.C.

(57) ABSTRACT

Methods of using unidirectionally propagating action potentials (UPAPs) for cavernous nerve stimulation and for certain disorders are provided. Stimulators capable of creating such UPAPs include, but are not limited to, miniature implantable stimulators (i.e., microstimulators), possibly with programmably configurable electrodes. In one aspect, a method includes providing at least one implantable stimulator with at least two electrodes, disposing the electrodes to apply stimulation that unidirectionally propagates action potentials along a cavernous nerve; and applying the stimulation to the cavernous nerve, thereby treating erectile dysfunction while limiting side effects of bidirectional stimulation.

19 Claims, 13 Drawing Sheets

U.S. PATENT DOCUMENTS

| | | | |
|---|---|---|---|
| 4,649,936 A * | 3/1987 | Ungar et al. | 607/118 |
| 4,702,254 A | 10/1987 | Zabara | 607/45 |
| 4,793,353 A | 12/1988 | Borkan | |
| 4,867,164 A | 9/1989 | Zabara | 607/45 |
| 5,188,104 A | 2/1993 | Wernicke et al. | |
| 5,193,539 A | 3/1993 | Schulman et al. | 607/61 |
| 5,193,540 A | 3/1993 | Schulman et al. | 607/61 |
| 5,199,430 A | 4/1993 | Fang et al. | 607/40 |
| 5,211,129 A | 5/1993 | Taylor et al. | 119/215 |
| 5,215,086 A | 6/1993 | Terry et al. | |
| 5,299,569 A | 4/1994 | Wernicke et al. | |
| 5,305,445 A | 4/1994 | Nishikawa | |
| 5,312,439 A | 5/1994 | Loeb | 607/2 |
| 5,314,458 A | 5/1994 | Najafi et al. | 607/116 |
| 5,324,316 A | 6/1994 | Schulman et al. | |
| 5,330,515 A | 7/1994 | Rutecki et al. | |
| 5,358,514 A | 10/1994 | Schulman et al. | 607/61 |
| 5,400,784 A | 3/1995 | Durand et al. | 600/377 |
| 5,405,367 A | 4/1995 | Schulman et al. | |
| 5,439,938 A | 8/1995 | Snyder et al. | 574/565 |
| 5,454,840 A | 10/1995 | Krakovsky et al. | 607/39 |
| 5,505,201 A | 4/1996 | Grill, Jr. et al. | 600/371 |
| 5,513,636 A | 5/1996 | Palti | 600/352 |
| 5,515,848 A | 5/1996 | Corbett, III et al. | 600/377 |
| 5,531,778 A | 7/1996 | Maschino et al. | 607/118 |
| 5,571,118 A | 11/1996 | Boutos | 607/138 |
| 5,571,148 A | 11/1996 | Loeb et al. | 607/56 |
| 5,634,462 A | 6/1997 | Tyler et al. | 600/377 |
| 5,649,970 A | 7/1997 | Loeb et al. | 607/57 |
| 5,700,282 A | 12/1997 | Zabara | 607/9 |
| 5,713,922 A | 2/1998 | King | 607/2 |
| 5,752,979 A | 5/1998 | Benabid | |
| 5,755,750 A | 5/1998 | Petruska et al. | |
| 5,775,331 A | 7/1998 | Raymond et al. | 600/554 |
| 5,895,416 A * | 4/1999 | Barreras et al. | 607/62 |
| 5,899,933 A | 5/1999 | Bhadra et al. | 607/118 |
| 5,938,584 A * | 8/1999 | Ardito et al. | 600/38 |
| 5,995,868 A | 11/1999 | Dorfmeister et al. | |
| 6,051,017 A | 4/2000 | Loeb et al. | 607/1 |
| 6,058,331 A | 5/2000 | King | 607/62 |
| 6,104,956 A | 8/2000 | Naritoku et al. | |
| 6,154,678 A | 11/2000 | Lauro | |
| 6,178,349 B1 | 1/2001 | Kieval et al. | |
| 6,198,970 B1 | 3/2001 | Freed et al. | 607/42 |
| 6,205,359 B1 | 3/2001 | Boveja | |
| 6,216,045 B1 | 4/2001 | Black et al. | |
| 6,226,552 B1 | 5/2001 | Staunton et al. | 607/72 |
| 6,266,564 B1 | 7/2001 | Hill et al. | |
| 6,341,236 B1 * | 1/2002 | Osorio et al. | 607/45 |
| 6,505,078 B1 | 1/2003 | King et al. | 607/67 |
| 6,526,318 B1 | 2/2003 | Ansarinia | |
| 6,560,490 B2 | 5/2003 | Grill et al. | 607/72 |
| 6,597,954 B1 | 7/2003 | Pless et al. | |
| 6,600,954 B2 | 7/2003 | Cohen et al. | 607/46 |
| 6,650,943 B1 | 11/2003 | Whitehurst et al. | |
| 6,712,753 B2 | 3/2004 | Manne | |
| 6,782,292 B2 | 8/2004 | Whitehurst | |
| 6,826,428 B1 | 11/2004 | Chen et al. | |
| 6,907,295 B2 | 6/2005 | Gross et al. | |
| 6,928,320 B2 | 8/2005 | King | |
| 7,054,692 B1 | 5/2006 | Whitehurst et al. | |
| 2001/0003799 A1 | 6/2001 | Boveja | |
| 2002/0016615 A1 | 2/2002 | Dev et al. | |
| 2002/0022873 A1 | 2/2002 | Erickson et al. | |
| 2002/0055779 A1 | 5/2002 | Andrews | 623/11.11 |
| 2002/0099256 A1 | 7/2002 | Manne | 600/9 |
| 2002/0099419 A1 | 7/2002 | Cohen et al. | 607/46 |
| 2002/0161415 A1 | 10/2002 | Cohen et al. | 607/48 |
| 2002/0193859 A1 | 12/2002 | Schulman et al. | 607/116 |
| 2003/0045909 A1 | 3/2003 | Gross et al. | 607/9 |
| 2003/0045914 A1 | 3/2003 | Cohen et al. | 607/62 |
| 2003/0050677 A1 | 3/2003 | Gross et al. | 607/72 |
| 2003/0083698 A1 | 5/2003 | Whitehurst et al. | |
| 2003/0100933 A1 | 5/2003 | Ayal et al. | 607/48 |
| 2003/0203890 A1 * | 10/2003 | Steiner et al. | 514/211.01 |
| 2003/0236558 A1 | 12/2003 | Whitehurst et al. | |
| 2004/0015204 A1 | 1/2004 | Whitehurst et al. | |
| 2004/0015205 A1 | 1/2004 | Whitehurst et al. | |
| 2004/0172089 A1 | 9/2004 | Whitehurst et al. | |
| 2004/0243182 A1 * | 12/2004 | Cohen et al. | 607/2 |
| 2004/0243185 A1 | 12/2004 | Weiss et al. | |
| 2005/0101878 A1 | 5/2005 | Daly et al. | |

FOREIGN PATENT DOCUMENTS

| | | |
|---|---|---|
| WO | WO-98/43700 A1 | 10/1998 |
| WO | WO-98/43701 A1 | 10/1998 |
| WO | WO-01/60445 A2 | 8/2001 |
| WO | WO-01/60445 A3 | 8/2001 |
| WO | WO-01/76690 A1 | 10/2001 |
| WO | WO-02/058782 A2 | 8/2002 |
| WO | WO-02/058782 A3 | 8/2002 |
| WO | WO-02/068042 A1 | 9/2002 |
| WO | WO-02/092165 A1 | 11/2002 |
| WO | 03/018113 | 3/2003 |
| WO | WO-03/018113 A1 | 3/2003 |

OTHER PUBLICATIONS

Bilgutay, et al., "Vagal Tuning: A New concept in the Treatment of Supraventricular Arrhythmias, Angina Pectoris, and Heart Failure", Journal of Thoracic and Cardiovascular Surgery, vol. 56, No. 1, (Jul. 1968), pp. 71-82.

Cameron, et al., "Micromodular Implants to Provide Electrical Stimulation of Paralyzed Muscles and Limbs", IEEE Transactions on Biomedical Engineering, vol. 44, No. 9, (Sep. 1997), pp. 781-790.

Lesser, et al., "Unexpected Places How did Vagus Nerve Stimulation Become a Treatment for Epilepsy?", Neurology, vol. 52, (1999), pp. 1117-1118.

Schoonhoven, et al., "The Inverse Problem in Electroneurography-I: Conceptual Basis and Mathematical Formulation", Biomedical Engineering, vol. 35(10), (1988), pp. 769-777.

Sweeney, et al., "An Asymmetric Two Electrode Cuff for Generation of Unidirectionally Propagated Action Potentials", IEEE Transactions on Biomedical Engineering, vol. BME-33, No. 6, (Jun. 1986), pp. 541-549.

Ungar, et al. "Generation of Unidirectionally Propagating Action Potentials Using a Monopolar Electrode Cuff", Annals of Biomedical Engineering, vol. 14(5), (1986), pp. 437-450.

Uthman, et al., "Treatment of Epilepsy by Stimulation of the Vagus Nerve", Neurology, vol. 43(1), (1993), pp. 338-345.

Van Den Honert, et al., "A Technique for Collision Block of Peripheral Nerve: Frequency Dependence", IEEE Transactions on Biomedical Engineering, vol. BME-28, No. 5, (May 1981), pp. 379-382.

Van Den Honert, et al., "A Technique for Collision Block of Peripheral Nerve: Single Stimulus Analysis", IEEE Transactions on Biomedical Engineering, vol. BME-28, No. 5, (May 1981), pp. 372-378.

Van Den Honert, et al., "Generation of Unidirectionally Propagated Action Potentials in a Peripheral Nerve by Brief Stimuli", Science, vol. 206, (Dec. 14, 1979), pp. 1311-1312.

Veraart, et al., "Selective Control of Muscle Activation with a Multipolar Nerve Cuff Electrode", IEEE Transactions on Biomedical Engineering, vol. 40, No. 7, (Jul. 1993), pp. 640-653.

U.S. Appl. No. 60/383,157 to Gross et al, filed May 23, 2002.

* cited by examiner

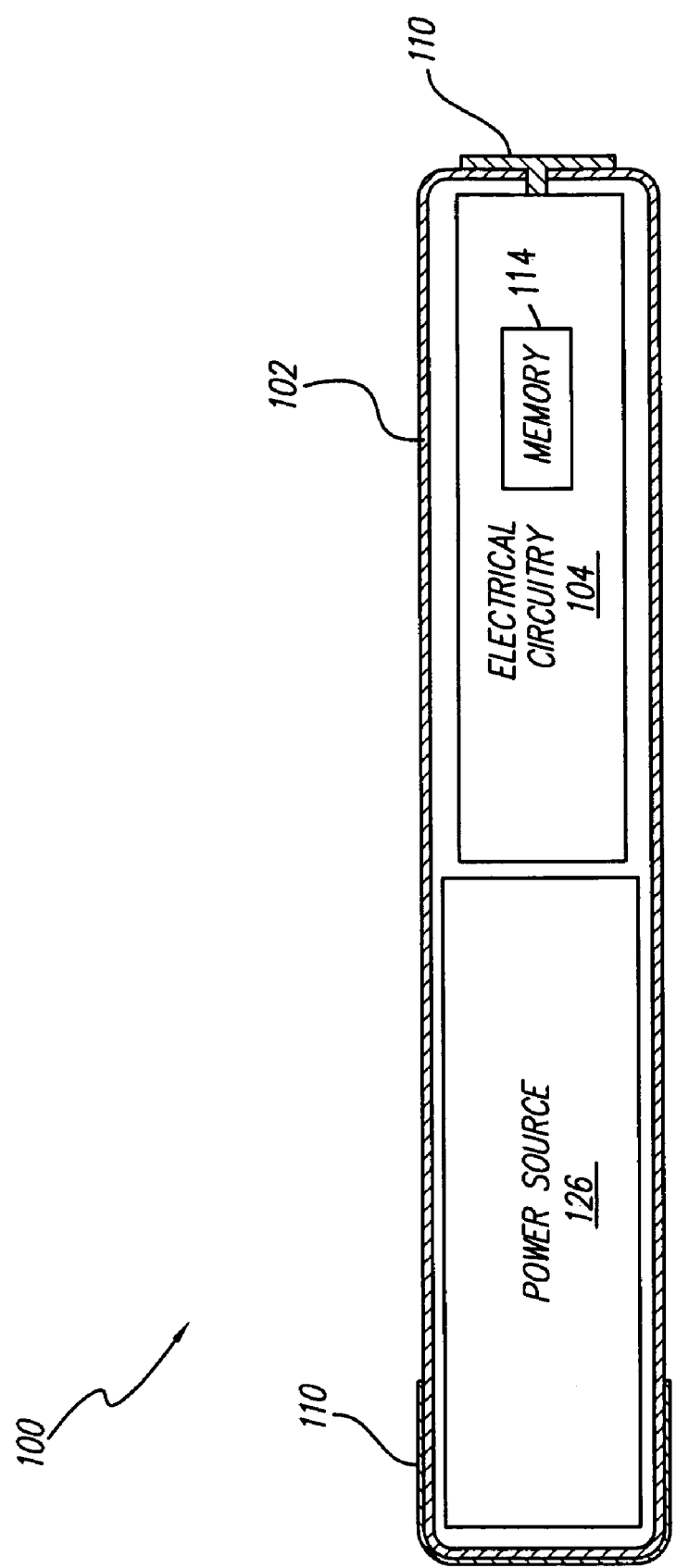

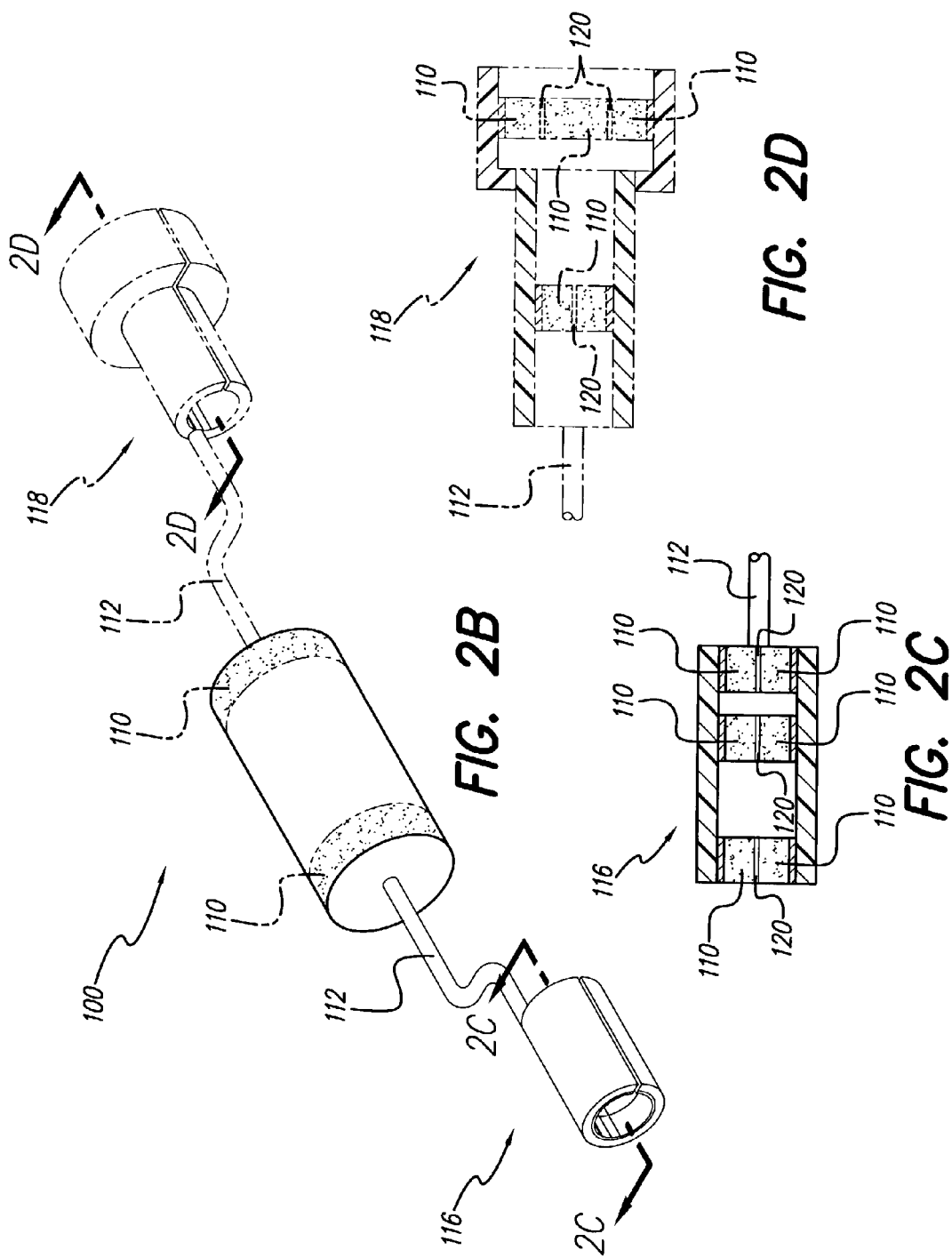

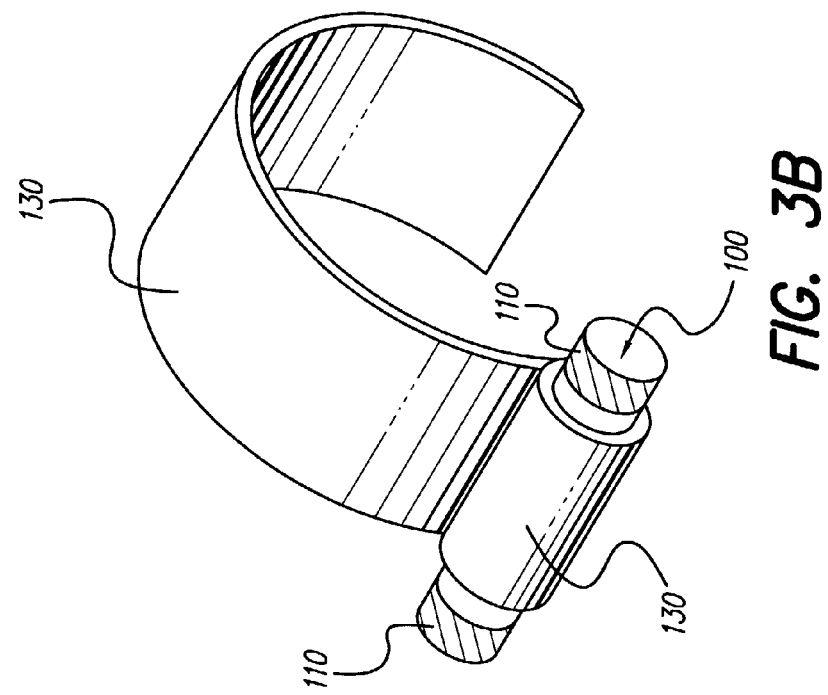
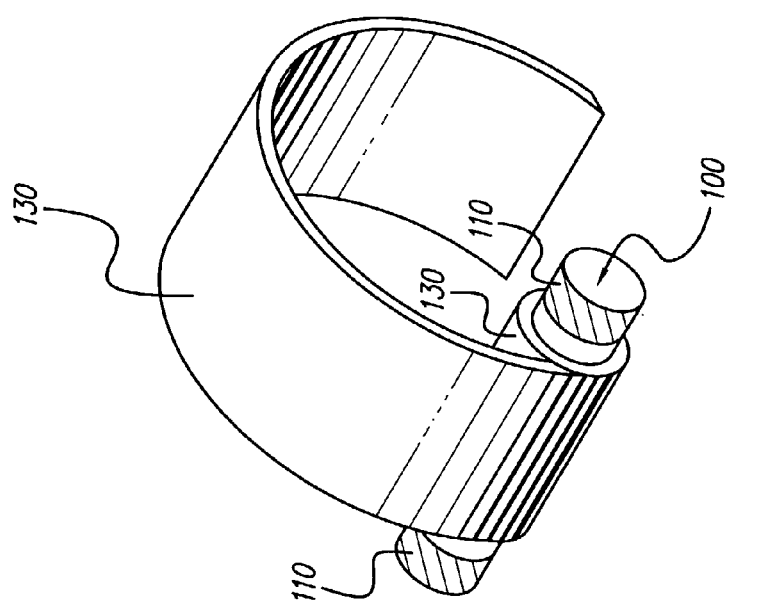
FIG. 3B
FIG. 3A

CAVERNOUS NERVE STIMULATION VIA UNIDIRECTIONAL PROPAGATION OF ACTION POTENTIALS

FIELD OF THE INVENTION

The present invention generally relates to implantable medical systems and methods, and more particularly relates to unidirectionally propagating action potentials of the cavernous nerve and uses thereof.

BACKGROUND OF THE INVENTION

Implantable electrical stimulation devices have proven therapeutic in a wide variety of diseases and disorders. Pacemakers and implantable cardiac defibrillators (ICDs) have proven highly effective in the treatment of a number of cardiac conditions (e.g., arrhythmias). Spinal cord stimulation (SCS) systems have long been accepted as a therapeutic modality for the treatment of chronic pain syndromes. Deep brain stimulation has also been applied therapeutically for well over a decade for the treatment of refractory chronic pain syndromes, and it has also recently been applied in additional areas such as movement disorders. In recent investigations, peripheral nerve stimulation (PNS) systems have demonstrated efficacy in the treatment of chronic pain syndromes, and a number of additional applications are currently under investigation. Finally, functional electrical stimulation (FES) systems such as the Freehand™ system by NeuroControl™ Corporation of Cleveland, Ohio have been applied to restore some functionality to paralyzed extremities in spinal cord injury patients.

Current implantable electrical stimulation systems typically consist of a system with electrodes on a lead, separate from but connected to an implantable pulse generator (IPG) that contains the power source and the stimulation circuitry. A number of these systems have multiple programmable electrodes, allowing each electrode to be configured as an anode, a cathode, or as an open circuit (i.e., electrically disconnected). However, these types of leaded systems have several disadvantages. The implantation procedure may be rather difficult and time-consuming, as the electrodes and the IPG must usually be implanted in separate areas and the lead must be tunneled through body tissue to connect to the IPG. Also, the leads are typically thin and rather long and are thus prone to mechanical damage over time. Additionally, many conventional systems typically consist of a relatively large IPG, which can have a negative cosmetic appearance if positioned subcutaneously.

Neurons typically propagate signals in one direction. Peripheral nerve fibers that propagate signals away from the central nervous system (CNS, i.e., the brain and the spinal cord) and towards the periphery and viscera are referred to as efferent nerve fibers. Peripheral nerve fibers that propagate signals away from the periphery and viscera and towards the CNS are referred to as afferent nerve fibers.

Efferent impulses may initiate a variety of actions, from movement of a muscle to initiation of changes in the heart rate or force of contraction or in the level of constriction of the vascular smooth muscle in arterioles. Through increasing or decreasing the activity of efferent fibers, the CNS can, for example, alter the blood pressure by changing the characteristics of the cardiovascular system.

Afferent impulses from specialized nerve endings or receptors inform the controlling neurons in the CNS about characteristics of the system, e.g., if a limb is feeling pain or if blood pressure is high or low. Most peripheral nerves contain both afferent and efferent nerve fibers.

A typical individual neuron consists of a soma (i.e., cell body), which contains the nucleus of the cell; dendrites, which receive input from pre-synaptic neurons; and an axon, which send signals via axon terminals (i.e., the distal portion of the axon) to post-synaptic neurons (or to effector cells, e.g., muscle fibers). An action potential is initiated at the initial segment of the axon (i.e., the proximal portion of the axon) when triggered by input from the dendrites. An action potential is an electrochemical signal that propagates from the initial segment down the axon to the axon terminals. Such propagation is referred to as orthodromic. (Orthodromic is defined as "of, relating to, or inducing nerve impulses along an axon in the normal direction.") Action potential propagation in the opposite direction is referred to as antidromic. (Antidromic is defined as "proceeding or conducting in a direction opposite to the usual one—used especially of a nerve impulse or fiber.")

In a neuron at rest, i.e., that is not propagating an action potential, the inside of the axon is negatively charged relative to the outside of the neuron, i.e., the membrane of the axon is at a negative resting potential.

When the soma receives sufficient stimulation at its associated dendrites, it initiates an action potential at the initial segment, which travels orthodromically down the axon. An action potential is initiated and propagated by opening channels in the axon membrane to allow positive charge (e.g., sodium ions) to enter the axon. This causes the voltage of the inside of the axon to become positive, i.e., it depolarizes a segment of the axon. Depolarization of one part of the axon causes depolarization of an adjacent patch of axon; this mechanism allows a wave of depolarization to sweep down the axon. After a brief period of depolarization (e.g., approximately 1 msec), the axon membrane automatically repolarizes to return to a resting state.

Electrical stimulation causes depolarization of the local axon membrane and may be used to initiate action potentials. For instance, electrical activation of an axon performed near the middle of an axon (i.e., not at the initial segment) produces two action potentials. One action potential propagates orthodromically, while the other propagates antidromically.

SUMMARY OF THE INVENTION

The invention disclosed and claimed herein addresses problems noted above and others by providing miniature implantable stimulators (i.e., microstimulators) with programmably configurable electrodes. In addition, to further address the above and other problems, the invention disclosed and claimed herein provides miniature implantable stimulators capable of unidirectional propagation of action potentials (UPAPs). Further, the instant disclosure teaches and claims methods of using UPAPs in certain locations and for certain disorders.

A microstimulator may be implanted via a small incision and/or via endoscopic means. A more complicated surgical procedure may be required for sufficient access to the nerve or portion of the nerve (e.g., nerve fibers surrounded by scar tissue) or for purposes of fixing the neurostimulator in place. A single microstimulator may be implanted, or two or more microstimulators may be implanted to achieve greater stimulation of the neural fibers.

The microstimulators used with the present invention possesses one or more of the following properties, among others:

at least two electrodes (e.g., one active electrode and one reference electrode) for applying stimulating current to surrounding tissue;

electrical and/or mechanical components encapsulated in a hermetic package made from biocompatible material(s);

an electrical coil or other means of receiving energy and/or information inside the package, which receives power and/or data by inductive or radio-frequency (RF) coupling to a transmitting coil placed outside the body;

means for receiving and/or transmitting signals via telemetry;

means for receiving and/or storing electrical power within the microstimulator; and a form factor making the microstimulator implantable via a minimal surgical procedure.

In some configurations, the microstimulator has at least three electrodes. In certain configurations, the microstimulator is leadless, while in others it may include electrodes on a relatively short lead. Additional microstimulator configurations are discussed in the detailed description of the invention.

Each electrode or section of a partitioned electrode may be configured via programming of stimulation parameters (i.e., programmably configured) as a cathode, an anode, or an open circuit with different current outputs. This allows the microstimulator to be "electrically positioned" once it has been implanted or otherwise fixed in place. This also allows the stimulation electrodes to be redefined via reprogramming of the stimulation parameters should the microstimulator migrate slightly. In turn, this allows stimulation to be directed to the appropriate site without needing to physically manipulate the microstimulator. Additionally, the use of the proper set(s) of electrodes allows more localized and selective stimulation of the target structures and reduces the magnitude of the injected electric current required to achieve neural stimulation, which results in less power consumed by the microstimulator.

A microstimulator may operate independently, or in a coordinated manner with other implanted devices, or with external devices. For instance, a microstimulator may incorporate means for sensing a patient's condition, which it may then use to control stimulation parameters in a closed loop manner. The sensing and stimulating means may be incorporated into a single microstimulator, or a sensing means may communicate sensed information to at least one microstimulator with stimulating means.

BRIEF DESCRIPTION OF THE DRAWINGS

The above and other aspects of the present invention will be more apparent from the following more particular description thereof, presented in conjunction with the following drawings wherein:

FIG. 1A is a section view through an exemplary, two-electrode microstimulator that may be used with certain embodiments of the present invention;

FIG. 2B is an isometric view of an exemplary microstimulator of the present invention, including one or more cuff electrodes;

FIG. 2C is a section view taken through 2C—2C of FIG. 2B;

FIG. 2D is a section view taken through 2D—2D of FIG. 2B;

FIGS. 3A and 3B show isometric views of microstimulators with fixation devices;

Corresponding reference characters indicate corresponding components throughout the several views of the drawings.

DETAILED DESCRIPTION OF THE INVENTION

Figure 1B:
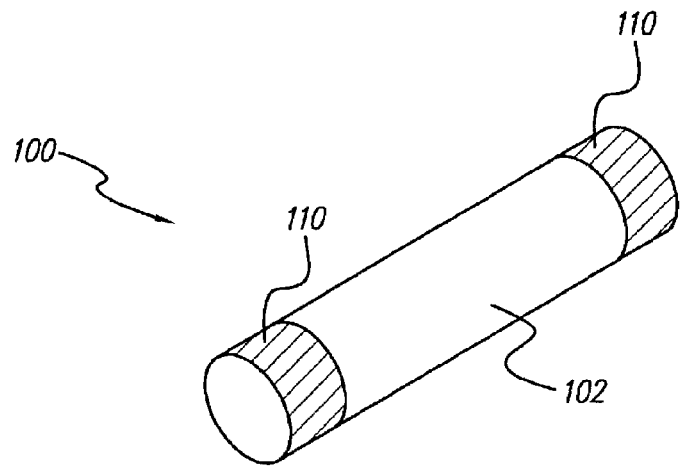
FIG. 1B is an isometric view of an exemplary, two-electrode microstimulator that may be used with certain embodiments of the present invention.

The following description is of the best mode presently contemplated for carrying out the invention. This description is not to be taken in a limiting sense, but is made merely for the purpose of describing the general principles of the invention. The scope of the invention should be determined with reference to the claims.

Unidirectionally Propagating Action Potentials (UPAPs)

As mentioned earlier, electrical activation of an axon usually produces action potentials that propagate in both the orthodromic and antidromic directions. Generation of a unidirectionally propagating action potential (UPAP) requires three essential components:

(1) Anodic Block in One Direction: Depolarization of an axon membrane leads to two action potentials traveling in opposite directions. In order to generate a UPAP, the propagation of one of the action potentials is blocked (i.e., arrested or inhibited), while the other is allowed to propagate. To block or arrest an action potential, a section of an axon membrane along the path of the undesired action potential is kept hyperpolarized during the time (or part of the time) the action potential would have traveled through that segment. To hyperpolarize the membrane, an electrode with anodic current is used. Therefore, to create a UPAP, the membrane must be depolarized at one electrode and hyperpolarized at another electrode. For instance, a cathodic current depolarizes the local axon membrane and initiates action potentials in opposing directions. A high anodic current may be used to hyperpolarize a section of axon membrane, thereby arresting action potential propagation in that direction.

Due to properties of the neurons, significantly less current is required to depolarize an axon enough to initiate an action potential than the current that is required to hyperpolarize an axon enough to arrest an action potential. Thus, the current that must be applied at the anode to arrest an action potential is typically higher in amplitude and of longer duration than that required for neurostimulation. Since the current flows between the cathode and the anode, this results in a relatively large cathodic current as well. This additional current requirement is not damaging to the cell or difficult to achieve. However, the generation of such high currents requires more energy from the neurostimulator and also requires electrodes with a relatively large surface area, so as to maintain safe levels of charge density and current density.

(2) Rebound Depolarization Control: Experimentally, if the very high anodic current used for hyperpolarization of the axon is discontinued abruptly, then the portion of the axon that was hyperpolarized suddenly depolarizes due to the non-linear properties of the axon membrane. In other words, if the hyperpolarizing anodic pulse is suddenly discontinued, the axon membrane can undergo a rebound depolarization (also known as anodic break) which may result in the generation of action potentials. Thus, to avoid rebound depolarization, the anodic current may be discontinued gradually, i.e., tapered off.

(3) Virtual Cathode Elimination: A nerve cuff is typically used for generation of UPAPs, as explained further presently. When a nerve cuff is used, it is desired that the current that flows between the anode and the cathode stay within the nerve cuff. However, some of the current inevitably flows from the anode, out of the nerve cuff, around the outside of the nerve cuff, and back in the other end, to the cathode. Since the hyperpolarizing current must be relatively large in magnitude, this "leakage" current is relatively high in magnitude as well. As this leakage current leaves the cuff at the end proximal to the anode, it effectively behaves as a "virtual cathode." (Under normal bi-directional stimulation conditions, the virtual cathode current is relatively low in amplitude, so it may not create sufficient depolarization to fire an action potential. Even if it does, with bi-directional stimulation the effect is likely to be indistinguishable from stimulation at the actual cathode.) In this case, the virtual cathode current is relatively high in amplitude, and thus can initiate an action potential. This is unwelcome, since the purpose of the nearby anode is to hyperpolarize the nerve and prevent action potential propagation in the direction of the anode. Different techniques have been used to eliminate the virtual cathode effect, including the introduction of an additional anode at the other end of the nerve cuff, as described in more detail presently.

Anodic Block in One Direction

Generating a UPAP requires that an unwanted propagating action potential be arrested (in one direction). A nerve containing nerve fibers of differing diameters and with differing conduction velocities may respond well to stimulation when the site of action potential initiation and site of arrest are closely spaced to minimize stimulus pulsewidth (and consequent charge injection). Such an arrangement may take the form of a conventional bipolar electrode configuration in a nerve cuff with the anode located at one end of the nerve cuff and the cathode located closer to the other end of the cuff.

Since the hyperpolarizing anodic current pulse is applied when the action potential is expected to reach the anode (or before), it is helpful if the spacing between the electrodes is known. Assuming a known velocity of action potential propagation in given nerve fibers, the time at which an action potential arrives at the anode may thus be predicted. Precise timing of the anodic pulse is also aided by known spacing between the electrodes and the nerve. Minimizing the spacing between the electrodes and the nerve reduces the current required for stimulation. In addition, fully enclosed cuffs concentrate the current near the nerve, reducing the amplitude of the required (cathodic and anodic) currents. In order to ensure that spacing is both controlled and minimized, a nerve cuff is typically used for UPAP; however, any arrangement in which the electrodes are closely apposed to the nerve, which also allows stimulation with less current, may be used for UPAP.

Virtual Cathode Elimination

UPAPs have been demonstrated in several experimental systems. In 1979, van den Honert and Mortimer demonstrated that single, unidirectionally propagated action potentials could be elicited in peripheral nerves by electrical stimuli of short duration. (See Van den Honert C; Mortimer J T "Generation of unidirectionally propagated action potentials in a peripheral nerve by brief stimuli" *Science* Dec. 14, 1979; 206(4424):1311–2.) They reduced the depolarizing effects of the virtual cathode using a tripolar electrode configuration; the center electrode was the cathode, and the two outside electrodes were anodes. The second anode created an additional electric field that opposed the flow of current from the first anode to the cathode through the path outside the cuff. Arresting (i.e., blocking or inhibiting) propagation of action potentials from both anodes was avoided by injecting a smaller current through the "escape" end anode than through the "arrest" end anode. This method required coordinated control of two stimulators. The stimulation pulse for UPAP was quasitrapezoidal in shape with a plateau pulsewidth of 350 μsec and an exponential trailing phase having a fall time of 350 μsec. The plateau amplitude necessary for UPAPs was 5–6 mA.

Other Methods of Generation of UPAP

In 1986, Ungar, et al. described a system for generation of UPAPs via a "collision block" in a cat myelinated peripheral nerve. (See Ungar I J; Mortimer J T; Sweeney J D "Generation of unidirectionally propagating action potentials using a monopolar electrode cuff." *Annals of Biomedical Engineering* 1986; 14(5):437–50.) This system used a monopolar electrode cuff with the conductor positioned closest to the "arrest" end of the cuff. A single cathode located at least 5 mm from the arrest end resulted in unidirectional propagation with minimal current and charge injection. The range of stimulus current values that produced unidirectional propagation increased with increases in longitudinal asymmetry of cathode placement over the range of asymmetries tested. The stimulus current pulse that minimized charge injection was quasitrapezoidal in shape with a plateau pulsewidth of approximately 350 μsec and an exponential trailing phase having a fall time of approximately 600 μsec. These stimulation parameters were found to be independent of cuff geometry. Arrest efficiency was not degraded using a cuff of sufficient internal diameter to prevent nerve compression in chronic implantation. The critical current density within the extracellular space of the electrode cuff required to produce conduction failure at the arrest end was estimated to be 0.47±0.08 mA/mm². The necessary total cuff length for effective unidirectional stimulation was from 32–48 mm.

Also in 1986, Sweeney, at al. described a system for generation of UPAPs using an asymmetric two-electrode cuff (ATEC). (See Sweeney J D; Mortimer J T "An asymmetric two electrode cuff for generation of unidirectionally propagated action potentials" *IEEE Transactions on Biomedical Engineering* 1986 June; 33(6):541–9.) This configuration differs from a standard bipolar cuff electrode in that the anode is enclosed by an insulating sheath of larger diameter than the cathode and the electrodes are asymmetrically placed within the cuff. The diameter of the cathode portion of the cuff was 16 mm and the diameter of the anode portion was as large as 26 mm. These electrodes were used to perform acute experiments in 13 adult cats. The stimulation pulse for UPAP was quasitrapezoidal in shape with a plateau pulsewidth of 200–500 μsec and an exponential trailing phase having a fall time of 400–1200 μsec. The plateau amplitude averaged 0.5 mA, and it varied from 0.1–2.3 mA. From the related dimensions specified in the article, it seems likely that the necessary total cuff length for effective unidirectional stimulation was less than 3 cm.

In the above studies, only cuff electrodes were used. In addition, the pulse generators used in these studies were not implantable, and as such, leads were used to enter the body and travel to the stimulation site(s). Use of the implantable systems and methods disclosed herein results in improved generation and delivery of UPAPs, among other improvements that will be evident to those of skill in the art upon review of the present disclosure.

The body reacts properly to orthodromic stimulation. Antidromic stimulation has a less significant physiological effect. UPAPs allow a system to effectively select afferent or efferent stimulation. For instance, when stimulating a nerve, if an action potential is allowed to escape in the direction of signals traveling away from the viscera and periphery and towards the CNS, both afferent and efferent fibers will transport the action potentials, but only the afferent fibers (with signals traveling orthodromically) will have an important physiological effect. Antidromic pulses on the efferent fibers will have a less significant physiological effect. This is referred to herein as "effective selection of afferent fibers." Correspondingly, "effective selection of efferent fibers" is performed via stimulation with UPAPs in the direction of signals traveling away from the CNS and toward the viscera and periphery, resulting in physiological effects via orthodromic pulses on the efferent fibers, while the antidromic pulses on the afferent fibers have a less significant physiological effect. Several applications of neuromodulation would benefit from neurostimulation applied to effectively select just the afferent or just the efferent nerves. Systems and methods described herein provide this ability.

For example, the vagus nerve provides the primary parasympathetic nerve to the thoracic organs (e.g., the lungs and heart) and most of the abdominal organs (e.g., the stomach and small intestine). It originates in the brainstem and runs in the neck through the carotid sheath with the jugular vein and the common carotid artery, and then adjacent to the esophagus to the thoracic and abdominal viscera. Through stimulation to effectively select afferent fibers (via UPAP stimulation traveling away from the viscera and the periphery and towards the CNS), unidirectional stimulation of the vagus nerve may be an effective treatment for a variety of disorders, including epilepsy and depression. Through stimulation to effectively select efferent fibers (via UPAP stimulation traveling away from the CNS and towards the viscera and the periphery), unidirectional stimulation of the vagus nerve may be an effective treatment for, e.g., tachycardia.

As yet another example, electrical stimulation of the cavernous nerve in the pelvis has been demonstrated to produce and sustain erection, and as such, is likely to prove an effective therapy for erectile dysfunction. The therapeutic effect is mediated by the efferent fibers, which stimulate structures in the corpora cavernosa and spongiosum of the penis. Stimulation of the afferent fibers of the cavernous nerve is likely to produce sensations that may be distracting, painful, or the like. Effectively selecting the efferent fibers of the cavernous nerve(s) as a therapy for erectile dysfunction could allow relatively higher levels of stimulation, which might provide more effective therapy for erectile dysfunction. This would also mitigate side effects such as pain at relatively high levels of stimulation.

The present invention provides, inter alia, microstimulator systems for stimulation of a nerve with unidirectionally propagating action potentials. In addition, the present invention provides programmably configurable multielectrode microstimulator systems. The present invention also provides improved treatments for various medical conditions, as mentioned above and described in more detail presently.

A microminiature implantable electrical stimulator, referred to herein as a microstimulator, and known as the BION® microstimulator, has been developed (by Advanced Bionics of Sylmar, Calif.) to overcome some of the disadvantages of traditional leaded systems. The standard BION is a leadless microstimulator, as the IPG and the electrodes have been combined into a single microminiature package. A standard configuration of the BION is a cylinder that is about 3 mm in diameter and between about 2 and 3 cm in length. This form factor allows the BION to be implanted with relative ease and rapidity, e.g., via endoscopic or laparoscopic techniques. With this configuration, the BION consists of only two electrodes: a reference, or indifferent, electrode at one end and an active electrode at the other end. In addition, with this configuration, electrical signals delivered to nerves travel away from the stimulation location along the nerve fibers in both directions.

The microstimulators of the present invention may be similar to or of the type referred to as BION devices. The following documents describe various features and details associated with the manufacture, operation, and use of BION implantable microstimulators, and are all incorporated herein by reference:

| Application/ Patent/ Publication No. | Filing/ Publication Date | Title |
|---|---|---|
| U.S. Pat. No. 5,193,539 | Issued Mar. 16, 1993 | Implantable Microstimulator |
| U.S. Pat. No. 5,193,540 | Issued Mar. 16, 1993 | Structure and Method of Manufacture of an Implantable Microstimulator |
| U.S. Pat. No. 5,312,439 | Issued May 17, 1994 | Implantable Device Having an Electrolytic Storage Electrode |
| U.S. Pat. No. 5,324,316 | Issued Jun. 28, 1994 | Implantable Microstimulator |
| U.S. Pat. No. 5,405,367 | Issued Apr. 11, 1995 | Structure and Method of Manufacture of an Implantable Microstimulator |
| U.S. Pat. No. 6,051,017 | Issued Apr. 18, 2000 | Improved Implantable Microstimulator and Systems Employing Same |
| PCT Publication WO 98/37926 | Published Sep. 3, 1998 | Battery-Powered Patient Implantable Device |
| PCT Publication | Published Oct. 8, 1998 | System of Implantable Devices For Monitoring and/or Affecting |

-continued

| Application/ Patent/ Publication No. | Filing/ Publication Date | Title |
|---|---|---|
| WO 98/43700 PCT Publication WO 98/43701 | Published Oct. 8, 1998 | Body Parameters System of Implantable Devices For Monitoring and/or Affecting Body Parameters |
| | Published September 1997 | Micromodular Implants to Provide Electrical Stimulation of Paralyzed Muscles and Limbs, by Cameron, et al., published in IEEE Transactions on Biomedical Engineering, Vol. 44, No. 9, pages 781–790. |

Figure 1C:
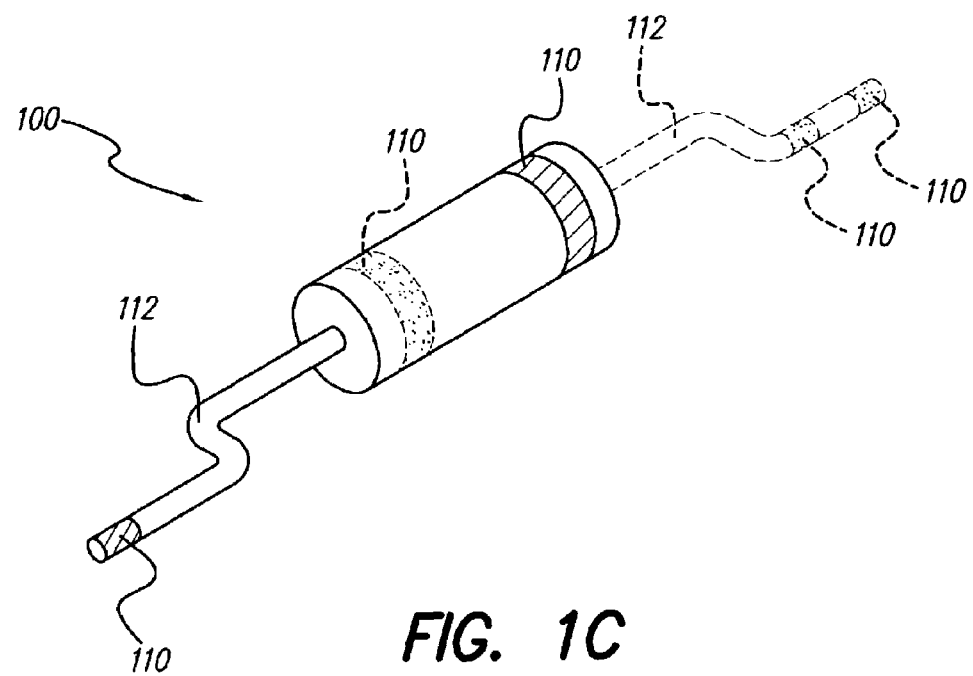
FIG. 1C is an isometric view of an exemplary, two or more electrode microstimulator that may be used with certain embodiments of the present invention.

As shown, for instance, in FIGS. 1A, 1B, and 1C, microstimulator device 100 may include a narrow, elongated capsule 102 containing electrical circuitry 104 connected to electrodes 110, which may pass through or comprise a part of the walls of the capsule, as in FIG. 1A. Alternatively, electrodes 110 may be built into the capsule (FIG. 1B) or arranged along a lead(s) 112 (FIG. 1C), as described below. As detailed in the referenced patent publications, electrodes 110 generally comprise a stimulating electrode, or cathode (to be placed close to the target tissue) and an indifferent electrode, or anode (for completing the circuit). Other configurations of microstimulator device 100 are possible, as is evident from the above-referenced publications, and as described in more detail herein.

Microstimulator 100 may be implanted via a minimal surgical procedure. Microstimulator 100 may be implanted with a surgical insertion tool specifically designed for the purpose, or may be placed, for instance, via a small incision and through an insertion cannula. Alternatively, microstimulator 100 may be implanted via conventional surgical methods, or may be inserted using other endoscopic or laparoscopic techniques. A more complicated surgical procedure may be required for sufficient access to a nerve or a portion of a nerve (e.g., nerve fibers surrounded by scar tissue, or more distal portions of the nerve) and/or for fixing the neurostimulator in place.

The external surfaces of microstimulator 100 may advantageously be composed of biocompatible materials. Capsule 102 may be made of, for instance, glass, ceramic, or other material that provides a hermetic package that will exclude water vapor but permit passage of electromagnetic fields used to transmit data and/or power. Electrodes 110 may be made of a noble or refractory metal or compound, such as platinum, iridium, tantalum, titanium, titanium nitride, niobium, or alloys of any of these, in order to avoid corrosion, electrolysis, or other electrochemical reactions which could damage the surrounding tissues and the device.

Microstimulator 100 contains, when necessary and/or desired, electrical circuitry 104 for receiving data and/or power from outside the body by inductive, radio-frequency (RF), or other electromagnetic coupling. In some embodiments, electrical circuitry 104 includes an inductive coil for receiving and transmitting RF data and/or power, an integrated circuit (IC) chip(s) for decoding and storing stimulation parameters and generating stimulation pulses (either intermittent or continuous), and additional discrete electrical components required to complete the electrical circuit functions, e.g. capacitor(s), resistor(s), coil(s), diode(s), and the like.

Microstimulator 100 includes, when necessary and/or desired, a programmable memory 114 (which may be a part of the electrical circuitry 104) for storing a set(s) of data, stimulation, and/or control parameters. Among other things, memory 114 may allow stimulation and control parameters to be adjusted to settings that are safe and efficacious with minimal discomfort for each individual. In addition, this allows the parameters to be adjusted to ensure that the stimulation favors unidirectional propagation, when desired. The device(s) may be implanted to deliver electrical stimulation to any location that is likely to be therapeutic, and the stimulation parameters may be adjusted to any set of parameters that prove efficacious, as described herein. Specific stimulation sites and parameters may provide therapeutic advantages for various medical conditions, their forms, and/or severity. For instance, some patients may respond favorably to intermittent stimulation, while others may require continuous stimulation to alleviate their symptoms. Therefore, various embodiments of the invention include means for providing stimulation intermittently and/or continuously.

Figure 2A:
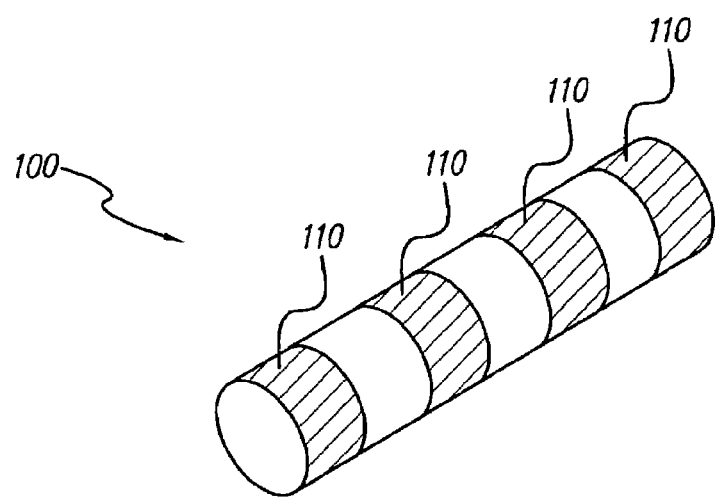
FIG. 2A is an isometric view of an exemplary microstimulator of the present invention, including a plurality of electrodes.

The present invention provides means of maintaining the advantages of earlier BION microstimulator systems while extending their functionality to enable, inter alia, programmably configurable multielectrode systems that allow current to be more effectively directed towards a target stimulation site. For instance, possible microstimulator configurations have one or more programmably configurable electrodes 110 arranged along the stimulator outer capsule, as shown in FIG. 2A. Thus, a microstimulator 100 may have a combination of programmably configurable and hard-wired electrodes, or may have only programmably configurable electrodes, or may have only a plurality of hard-wired electrodes.

The configuration of microstimulator 100 may be determined by the structure of the desired target, the surrounding area, and the method of implantation. The size and the shape of the microstimulator may be varied in order to deliver more effective treatment. A thin, elongated cylinder with electrodes at the ends and/or along the cylindrical case are possible configurations, but other shapes, such as disks, spheres, helical structures, and others are possible. Additional alterations in configuration, such as the number, orientation, and shape of electrodes (which may be programmably configurable), may be varied in order to deliver more effective treatment. For instance, the electrodes may be rectangular, semi-spherical, arcs, bands/rings, or any other useful shape, and may be distributed along and/or around the surface of the microstimulator.

Implantable microstimulator 100 is sufficiently small to permit its placement in or near the structures to be stimulated. For instance, capsule 102 may have a diameter of about 4–5 mm, or only about 3 mm, or even less than 3 mm. Capsule 102 length may be about 25–40 mm, or only about 20–25 mm, or even less than 20 mm. In some configurations and for some stimulation sites, it may be useful for microstimulator 100 to be larger, to be of a different shape, or to include a lead(s) 112, as described in more detail below.

In some embodiments of the instant invention, microstimulator 100 comprises two or more leadless electrodes. However, one or more electrodes 110 may alternatively be located along short, flexible leads 112 (FIG. 1C) as described in U.S. patent application Ser. No. 09/624,130, filed Jul. 24, 2000, which is incorporated herein by reference in its entirety. The use of such leads permits, among other things, electrical stimulation to be directed more locally to targeted tissue(s) a short distance from the surgical fixation of the bulk of the implantable microstimulator 100, while allowing most elements of the microstimulator to be located in a more surgically convenient site and/or in a position making telemetry with and/or powering and/or replacing or removing the device simpler. This minimizes the distance traversed and the surgical planes crossed by the device and any lead(s). Other uses of such configurations will be apparent presently. For instance, the electrodes may be positioned on a cuff(s) attached to the microstimulator via a lead(s), as described below. In most uses of this invention, the leads are no longer than about 150 mm.

A microstimulator including a cuff electrode, as shown in FIGS. 2B, 2C, and 2D, may be a tripolar cuff electrode 116, possibly with an asymmetric placement of the center electrode. The electrodes may substantially form a ring, or the electrodes may be partitioned. Other cuff electrode configurations, as known to those of skill in the art, may alternatively or additionally be used. Such a cuff electrode may be a bipolar cuff electrode 118 with the anode placed farther from the nerve than the cathode via the use of an insulating sheath of larger diameter for the anode than the cathode.

According to one embodiment of the invention, a microstimulator is attached to the cuff electrode via a lead 112. According to another embodiment of the invention, the cuff electrode is incorporated into the microstimulator package, e.g., a microstimulator with a cuff electrode attachment or other microstimulator fixation device 130, as in U.S. patent application Ser. No. 10/146,332 (the '332 application), which application is incorporated herein by reference in its entirety. As discussed in the '332 application, fixation device 130 may include one or more electrodes 110. Examples of microstimulator cuff electrode attachments/fixation devices 130 that may be used with the present invention are shown in, but not limited to, FIGS. 2B, 2C, 2D, 3A, 3B, and 3C.

In some applications, a microstimulator having a single cathode may be sufficient. For instance, in some applications, such as pudendal nerve stimulation for urge incontinence, the target may be rather large in at least one dimension, allowing for some positioning error. However, for some applications, a single cathode microstimulator may prove insufficient or imperfect. For instance, if a target site is very small in all dimensions, the microstimulator may be difficult to place precisely. For example, in deep brain stimulation for Parkinson's disease, the subthalamic nucleus has a maximum dimension of only 4–7 mm. Precisely placing the microstimulator at this target is likely to be difficult, and even slight migration of the microstimulator over time may reduce its efficacy. Other stimulation target sites may be physically constrained, so that the microstimulator cannot be or is difficult to position ideally in relation to the stimulation target. For example, the trigeminal ganglion, which receives sensation from all of the sensory nerves of the face, sits in a dural compartment known as the trigeminal (Meckel's) cave, which lies in a depression on the anterior slope of the petrous portion of the temporal bone. The trigeminal cave is a rather confined space that is surrounded by bone, and a solid device, even a microstimulator, may not be easy to manipulate and precisely position in such a space.

In addition, in configurations where the microstimulator electrodes are cylindrical (either on a lead or on the case of a cylindrical microstimulator), the stimulation current is generally directed 360 degrees radially outward. However, the target neurons may be located only to one side of the electrode(s). Such a situation can result in higher thresholds (due to wasted current directed away from the neural targets) as well as undesired stimulation of neurons that are not the desired targets of stimulation. Solutions to this problem may involve locating the electrodes to one side of the array. However, lead or microstimulator migration or rotation can make such designs ineffective or cumbersome to deploy and maintain.

The programmably configurable multielectrode microstimulators of the present invention, which can be "electrically positioned" as described herein, address these and other problems. In certain embodiments, such as shown in FIG. 2A, the microstimulator has a cylindrical shape, with electrodes 110 configured as a plurality of anodes, cathodes, and/or open circuit electrodes distributed along its surface. One or both ends may be capped with an electrode 110, and one or more electrodes may be arranged along the microstimulator outer case.

Figure 2E:
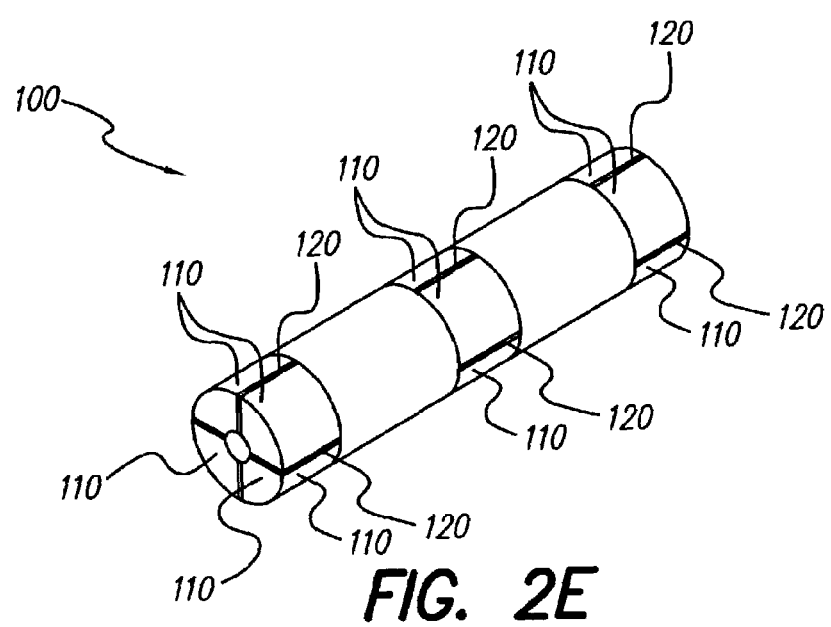
FIG. 2E is an isometric view of an exemplary microstimulator of the present invention, including a plurality of partitioned electrodes.
Figure 3C:
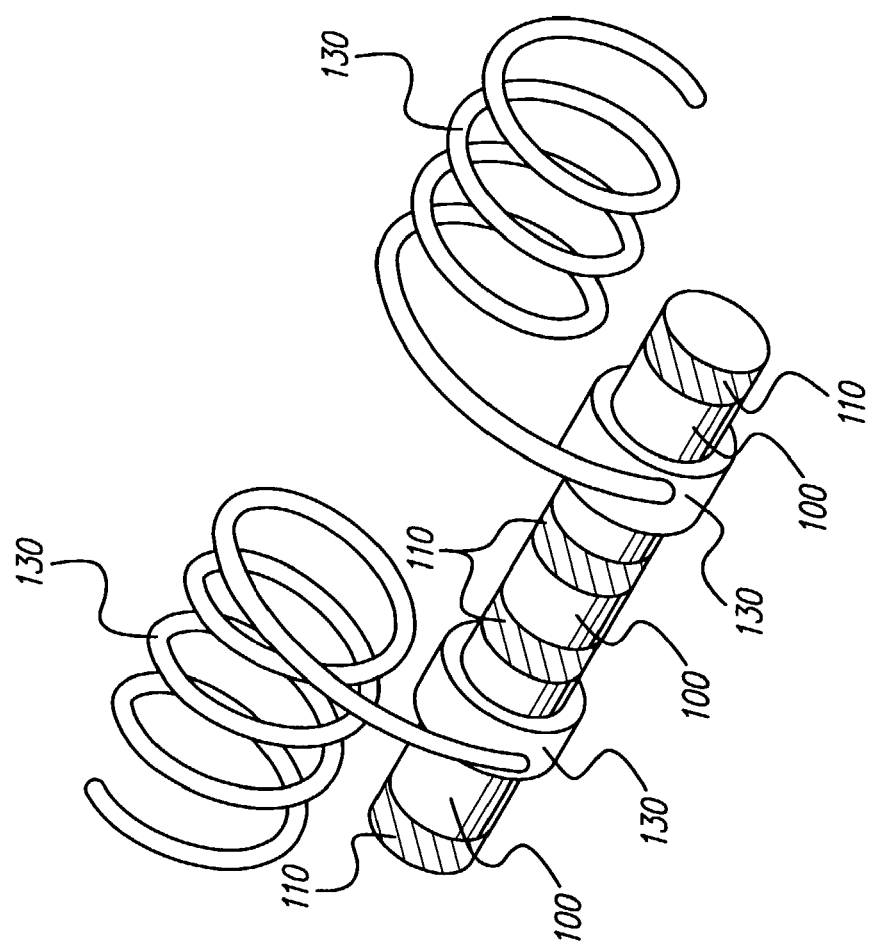
FIG. 3C depicts a microstimulator with a fixation device that includes helices that wrap around a nerve or other body tissue.

In various embodiments, the end cap electrode(s) and/or those along the length of the microstimulator and/or those on a lead attached to a microstimulator can be further divided as shown in FIG. 2E into "partitioned" electrodes. Thus, individual electrodes, rather than extending completely around the microstimulator, are partitioned into short arcs. In between each of the partitioned electrodes 110 is an insulating material 120 to provide some electrical isolation. In an extreme alternative, the microstimulator could be covered with small arcs of electrodes along its entire surface. The size of the electrodes 110 and the insulating areas 120 may be uniform or may be independent and varied.

Electrodes configured along and/or around the microstimulator can be individually programmed via stimulation parameters into various configurations to "steer" the electric field radially around the microstimulator (e.g., activating cathode(s) and anode(s) positioned substantially radially around the microstimulator) and/or longitudinally along the microstimulator (e.g., activating cathode(s) and anode(s) positioned substantially linearly along the microstimulator); such a microstimulator can be "electrically positioned." A relatively large number of small independent electrodes allows the electric field to be programmed in many configurations, such as very wide fields (e.g., multiple grouped cathodes and anodes) or very narrow fields (e.g., single electrodes for one cathode and one anode, using adjacent electrodes). Such electrode array designs can mimic the electrode design of FIGS. 1A, 1B, and/or 2A, for instance, while still allowing the more focal stimulation from choosing individual electrodes.

Steering of the electric field (a.k.a., electrically positioning the stimulator) can be achieved by programming the stimulation parameters to activate different electrodes and program each activated electrode as a cathode, an anode, or an open circuit, as well as by controlling the current flowing from each electrode that is activated. Such steering capability allows the electric field to be located more precisely to target desired neurons, minimizing stimulation thresholds needed to capture the desired neural targets, thus minimizing power consumption of the stimulator. Also, if microstimulator 100 or lead 112 happens to rotate or migrate, some designs allow the electric field to be reprogrammed by adjusting the stimulation parameters, thus allowing the microstimulator to be electrically positioned without having to physically manipulate and reposition the microstimulator or electrodes.

All or some cathodes may be electrically connected, or some or all of the cathodes may be independently driven individually or in configurable groups, i.e., the stimulator may have multiple stimulation channels. Similarly, all or some anodes may be electrically connected, or some or all of the anodes may be independently driven individually or in configurable groups. In some embodiments, at least one electrode is a dedicated anode, and in various embodiments, at least one electrode is a dedicated cathode.

In certain embodiments, microstimulator 100 is capable of producing waveforms that can cause electrical stimulation and activation of neural fibers. Such a waveform includes a periodic asymmetric square wave pulse that consists of an initial cathodic pulse followed by a programmable delay with minimal or no current and ending with an anodic charge recovery pulse. Between stimulation pulses, the output of a given electrode consists of minimal and ideally no current. Other waveforms, including but not limited to trapezoidal and exponential, may be used. In some such nerve stimulation embodiments, the stimulator produces pulses in the range from about 10 µA to about 15 mA, with a compliance voltage from about 0.05 volts to about 20 volts, a pulsewidth range from about 10 µsec to about 4.0 msec, and a stimulation frequency range from about 1 pulse per second (pps) to about 10,000 pps.

Certain embodiments include means for producing a biphasic stimulation periodic pulse waveform with a programmable stimulation phase pulsewidth in the range of about 50 µsec to about 5 msec and a charge recovery phase having a programmable pulsewidth in the range of about 50 µsec to about 5 msec. The biphasic stimulation periodic pulse waveform may be symmetric or asymmetric. The shapes of these waveforms may be any of those known to those of skill in the art. For example, the stimulation pulse may be a square pulse, and the charge recovery pulse may be a square pulse, or it may be a trapezoidal or quasitrapezoidal pulse.

Some embodiments of the present invention, such as those producing UPAPs, include means for producing a stimulation pulse with, e.g., a quasitrapezoidal shape, with a programmable plateau pulsewidth in the range of about 10 µsec to about 5 msec, and a decaying trailing phase (e.g., an exponentially decaying trailing phase) having a programmable fall time in the range of about 50 µsec to about 5 msec. The stimulation pulse may be a square pulse, a trapezoidal or triangular pulse, or any other shape known to those of skill in the art. The charge recovery pulse may be a square pulse, a trapezoidal or quasitrapezoidal pulse, or any other shape known to those of skill in the art, with, e.g., a plateau pulse width of about 50 µsec to about 10 msec. As described earlier, this anodic charge recovery pulse may be tapered to avoid rebound depolarization and generation of additional action potentials. As such, the anodic pulse with, for instance, a trapezoidal or quasitrapezoidal pulse, may have a decaying trailing phase (e.g., an exponentially decaying trailing phase) with a programmable fall time in the range of about 50 µsec to about 5 msec.

In some embodiments, part or all of the charge recovery pulse may precede the stimulation pulse. In certain embodiments, the charge recovery pulse entirely precedes the stimulation pulse. In various embodiments, a charge recovery pulse precedes the stimulation pulse and an additional charge recovery pulse follows the stimulation pulse.

If a tripolar or other multipolar electrode configuration is used (e.g., a tripolar nerve cuff), then means for distributing the current asymmetrically between the electrodes may be included, i.e., the polarities and currents of the electrodes may be independently programmable. For example, in a nerve cuff with one cathode and two anodes, the anodic currents may be independently programmed to be of different amplitudes.

The BION microstimulators described in the earlier referenced patents and publications require some architectural modifications in order to provide UPAP. The microstimulators 100 of the present invention configured to provide UPAP include, in some embodiments, at least three electrodes 110, and more specifically, at least one cathode and at least two anodes (which may be configured as such by the programmable stimulation parameters). The electrodes may be distributed collinearly along the long axis of the microstimulator, with the at least one cathode in between the at least two anodes. In some embodiments, the electrodes surround the microstimulator radially. In alternative embodiments, the electrodes may be segmented such that an individual electrode extends part way around the microstimulator; this should provide more focal application of cathodic and/or anodic currents.

In various embodiments, one or more of the electrodes may be a "virtual" electrode, for instance, when a microstimulator with a fixation device such as a nerve cuff is used. A nerve cuff is typically used to maintain the electrodes in close proximity to a specific target tissue and to maintain a larger density of injected charge in the target area within the cuff. However, some of the current inevitably flows around the outside the cuff. When this happens, the edges of the cuff behave as "virtual" electrodes. The virtual electrodes typically have a polarity opposite that of the "real" electrodes that create the current flowing around the edge of the cuff. These virtual electrodes can stimulate tissue, as do real electrodes.

For example, a single real anode inside a nerve cuff with a reference electrode outside the cuff will behave similar to a tripolar cuff electrode with real cathodes on either side of a real anode. As injected electric current from the anode flows towards the reference electrode (which is located external and typically relatively distant from the cuff), the current is forced to leave the cuff at the edges since the cuff is less electrically conducting than the tissue. As perceived by the tissue inside the cuff, the edges of the cuff appear to behave as sinks of current, thus creating virtual cathodes at the edges of the cuff. Similarly, if the single electrode in the cuff is a cathode, the edges of the cuff will behave as anodes.

The amount of current and current density that flows through the edges of the cuff will determine the relative strength of the virtual electrodes. Different means can be used to control the relative strength of the virtual electrodes. For instance, by placing a single electrode asymmetrically within the cuff and a reference electrode symmetrically outside the cuff, a stronger virtual electrode (more current) will typically be created on the edge of the cuff that is closer to the real electrode. As another example, by placing the reference electrode asymmetrically outside the cuff and the real electrode symmetrically within the cuff, a stronger virtual electrode (more current) will be created on the edge of the cuff that is closer to the reference electrode. As yet another example, by increasing the diameter of one side of the cuff, the virtual electrode on that side can be made relatively weaker. Similarly, by decreasing the diameter of one side of the cuff, the virtual electrode on that side can be made relatively stronger. These and other means to control the relative strength of virtual electrodes can be combined to allow for further control of the relative strength of the virtual electrodes.

As described above, due to the presence of virtual electrodes, systems with a given number of real electrodes can behave like systems with a greater number of electrodes. For instance, a system with a single real electrode, such as a single real cathode placed asymmetrically within a nerve cuff or a single real cathode placed asymmetrically on a microstimulator with a fixation device, can be used to generate UPAPs. The edge of the cuff/fixation device closer to the real electrode will be a stronger virtual anode than the edge of the cuff/fixation device further from the real electrode. Therefore, propagation of action potentials created by the cathode can be arrested by the stronger virtual anode but allowed to propagate past the weaker virtual anode. Previously described methods for controlling the relative strength of the virtual anodes can also be used in single real electrode UPAP generating systems. For purposes of this description and the claims defining the scope of the invention, virtual and real electrodes are both encompassed by the term "electrodes". Therefore, for instance, this single real electrode UPAP generating system comprises at least three electrodes: the "real" cathode and two "virtual" anodes. Similarly, where herein reference is made to "a cathode" or "an anode" the cathode and/or anode may be "real" or "virtual".

UPAPs can also be produced with systems containing only two real electrodes. For instance, the asymmetric two-electrode cuff (ATEC) system described earlier used a larger cuff diameter at the anode side of the cuff and asymmetrically placed the anode and cathode within the cuff. This configuration reduced the relative strength of the virtual cathode, thereby reducing the depolarizing effects of the virtual cathode. Similarly, a microstimulator with a fixation device, even one with only two electrodes, can be configured to produce UPAPs. In configurations where the anode and cathode share a power source, the current that depolarizes the nerve at the cathode hyperpolarizes the nerve fibers at the anode. In configurations including, e.g., a reference electrode, an anode, a cathode, and more than one power source, the hyperpolarizing current may be, for instance, of longer duration and/or higher in amplitude than the depolarizing current. These anodes and cathodes may be real or virtual. Methods described above for reducing the relative strength of a virtual cathode can also be used in UPAP systems with two real electrodes.

Virtual electrodes can also be used to reduce the effect of other virtual electrodes. A virtual cathode may be eliminated with the addition of an anode on the opposite side of the cuff from the virtual cathode. This extra anode can also be a virtual anode. Additionally or alternatively, the virtual cathode can be addressed with the methods described above for controlling the relative strength of virtual electrodes. For instance, in a two "real" electrode cuff system, a virtual cathode appears on the edge of the cuff near the real anode, while a virtual anode appears on the side near the real cathode. By placing the real electrodes asymmetrically within the cuff, in such a way that the real anode is further from the edge of the cuff than the real cathode, the relative strength of the virtual anode will increase and the relative strength of the virtual cathode will diminish. This system with two real electrodes will effectively produce UPAPs in the direction of the real cathode, while arresting propagation in the direction of the real anode.

As mentioned earlier, a microstimulator may include or be attached to a fixation device that holds the microstimulator and/or electrodes in close apposition to the nerve. Among other things, this may help control the spacing desired between the electrodes and target nerve. For example, the microstimulator might include or be integrated as part of a nerve cuff. Various embodiments of this invention include a cuff electrode assembly that allows UPAPs. Such a device may be a tripolar cuff electrode 116 (FIG. 2B), possibly with an asymmetric placement of the center (cathodic) electrode. Other cuff electrodes can be as described above, where one or more of the electrodes is a virtual electrode. According to some embodiments of the invention, a microstimulator as in the '332 application, with examples shown in FIGS. 3A–3C, includes a fixation device 130. Once again, one or more of the electrodes may be a virtual electrode. According to other embodiments, a microstimulator is attached to one or more cuff electrodes via a lead, as in FIG. 2B.

The microstimulator may also include means for simultaneously providing anodic current of different amplitude through two or more different anodes. For example, when a microstimulator with a nerve cuff or the like is used, this allows one anode to be used to produce a relatively high amplitude hyperpolarizing anodic current, while another anode may be used to produce a relatively low amplitude anodic current to shunt some of the current that leaks outside the nerve cuff, thereby preventing depolarization and stimulation by a virtual cathode. In some such embodiments, the means includes two different current sources with a common cathode and different anodes. In some embodiments, the means includes programmable stimulation parameters. In some embodiments, the means includes two or more microstimulators.

The present invention also provides means for unidirectional propagation of action potentials in a selected subset(s) of neurons by taking advantage of the fact that the speed of an action potential depends on the diameter of a neuron. For instance, as is known in the art, the relatively large diameter A-α fibers (up to about 22 micron diameter) conduct action potentials at up to about 120 m/sec, while the relatively small diameter C fibers (up to about 1 micron diameter) conduct action potentials at up to about 2 m/sec. As used herein, large diameter fibers means relatively large diameter nerve fibers, and includes A-α, A-β, and A-γ fibers, while small diameter fibers means relatively small diameter nerve fibers, and includes A-δ, B, and C fibers. Through appropriate timing, an action potential may be passed along one size fiber and may be arrested in another.

For example, action potentials in large diameter afferent fibers travel relatively faster than in small diameter afferent fibers. A relatively high-amplitude depolarizing current is applied to the nerve to initiate bi-directional action potentials in both small and large diameter nerve fibers. To arrest afferent propagation of action potentials in small diameter fibers, relatively high-amplitude hyperpolarizing anodic current is applied at the anode after the large diameter action potentials has passed (or has at least been initiated) and before the action potentials in the small diameter fibers has been initiated (or at least before it has passed). Thus, some or all of the action potentials in the small diameter afferent fibers would be arrested. To do this would likely require the electrodes to be spaced relatively far apart, for instance, with one or more microstimulators or with electrodes on leads attached to a microstimulator(s).

Similarly, action potentials in large diameter efferent fibers travel relatively faster than in small diameter efferent fibers. Again, a relatively high-amplitude depolarizing current is applied to the nerve to initiate bi-directional action potentials in both small and large diameter nerve fibers. To arrest efferent propagation of action potentials in small diameter fibers, once again, relatively high-amplitude hyperpolarizing anodic current is applied at the anode after the large diameter action potentials has passed (or has at least been initiated) and before the action potentials in the small diameter fibers has been initiated (or at least before it has passed). Thus, some or all of the action potentials in the small diameter efferent fibers would be arrested. As above, electrodes spaced relatively far apart, such as electrodes on leads attached to one or more microstimulators, would likely be required.

In another example, the present invention provides means for arresting propagation of action potentials in small and large diameter fibers in one direction along a nerve. As in the examples above, a relatively high-amplitude depolarizing current is applied to the nerve to initiate bi-directional action potentials in both small and large diameter nerve fibers. As used herein, a relatively high-amplitude depolarizing current is applied at an amplitude of about 0.01 mA to about 15 mA, with a pulse width of about 0.01 msec to about 5.0 msec. To arrest propagation of action potentials in small and large diameter fibers, a hyperpolarizing anodic current(s), which is of relatively high-amplitude, is applied at the anode before the action potentials in the small and large diameters fibers has passed. As used herein, relatively high-amplitude hyperpolarizing anodic current is applied at an amplitude of about 0.1 mA to about 15 mA, with a pulse width of about 0.1 msec to about 10.0 msec. In this and the examples above, the anodic current may be tapered at the end in order to reduce the likelihood of a rebound stimulation of an action potential, as described earlier. Apply additional anodic current(s) as needed to prevent stimulation at a virtual cathode.

As yet another example, the present invention provides means for arresting propagation of action potentials in large diameter fibers. A relatively large cathodic current can initiate a bi-directional action potential in both small diameter and large diameter fibers. However, a relatively low-amplitude hyperpolarizing anodic current is more likely to hyperpolarize a large diameter fiber than a small diameter fiber and is thus more likely to cause anodic block and arrest of action potential propagation in a large fiber. Thus, in order to selectively arrest action potentials in large diameter fibers while allowing propagation of action potentials in small diameter fibers, the following steps may be followed:

1) Apply a relatively high-amplitude depolarizing cathodic current to the nerve. This will depolarize axons of all sizes and will thus initiate bi-directional action potentials in both small and large nerve fibers.
2) On the side(s) of the cathode on which arrest is desired, apply a relatively low-amplitude hyperpolarizing anodic current to the nerve. As used herein, relatively low-amplitude hyperpolarizing anodic current is applied at an amplitude of about 0.01 mA to about 10 mA, with a pulse width of about 0.01 msec to about 5.0 msec. This current should be sufficient to hyperpolarize and arrest action potentials in large fibers but not in small fibers, as large fibers are more easily hyperpolarized than small fibers. Once again, the anodic current may be tapered at the end to reduce the likelihood of rebound stimulation.
3) Apply additional anodic current(s) simultaneously with the steps above as needed to prevent stimulation at a virtual cathode.

Stimulation parameters may have different effects on different neural tissue, and parameters may be chosen to target specific neural populations and to exclude others, or to increase neural activity in specific neural populations and to decrease neural activity in others. As an example, relatively low frequency stimulation (i.e., less than about 50–100 Hz) typically has an excitatory effect on surrounding neural tissue, leading to increased neural activity, whereas relatively high frequency stimulation (i.e., greater than about 50–100 Hz) may have an inhibitory effect, leading to decreased neural activity. Therefore, low frequency electrical stimulation may be used to increase electrical activity of a nerve by increasing the number of action potentials per second in either one direction or in both directions. As yet another example, a relatively low-amplitude stimulation current is more likely to initiate an action potential in large diameter fibers, while a relatively high-amplitude stimulation current is more likely to initiate an action potential in both large and small diameter fibers.

Some embodiments of implantable microstimulator 100 include a power source and/or power storage device 126. Possible power options for a microstimulator of the present invention include, but are not limited to, an external power source coupled to the stimulation device, e.g., via an RF link, a self-contained power source utilizing any suitable means of generation or storage of energy (e.g., a primary battery, a replenishable or rechargeable battery such as a lithium ion battery, an electrolytic capacitor, a super- or ultra-capacitor, or the like), and if the self-contained power source is replenishable or rechargeable, means of replenishing or recharging the power source (e.g., an RF link, an optical link, a thermal link, or other energy-coupling link).

According to certain embodiments of the invention, a microstimulator operates independently. According to various embodiments of the invention, a microstimulator operates in a coordinated manner with other microstimulator(s), other implanted device(s), or other device(s) external to the patient's body. For instance, a microstimulator may control or operate under the control of another implanted microstimulator(s), other implanted device(s), or other device(s) external to the patient's body. A microstimulator may communicate with other implanted microstimulators, other implanted devices, and/or devices external to a patient's body via, e.g., an RF link, an ultrasonic link, a thermal link, an optical link, or the like. Specifically, a microstimulator may communicate with an external remote control (e.g., patient and/or physician programmer) that is capable of sending commands and/or data to a microstimulator and that may also be capable of receiving commands and/or data from a microstimulator.

Figure 4:
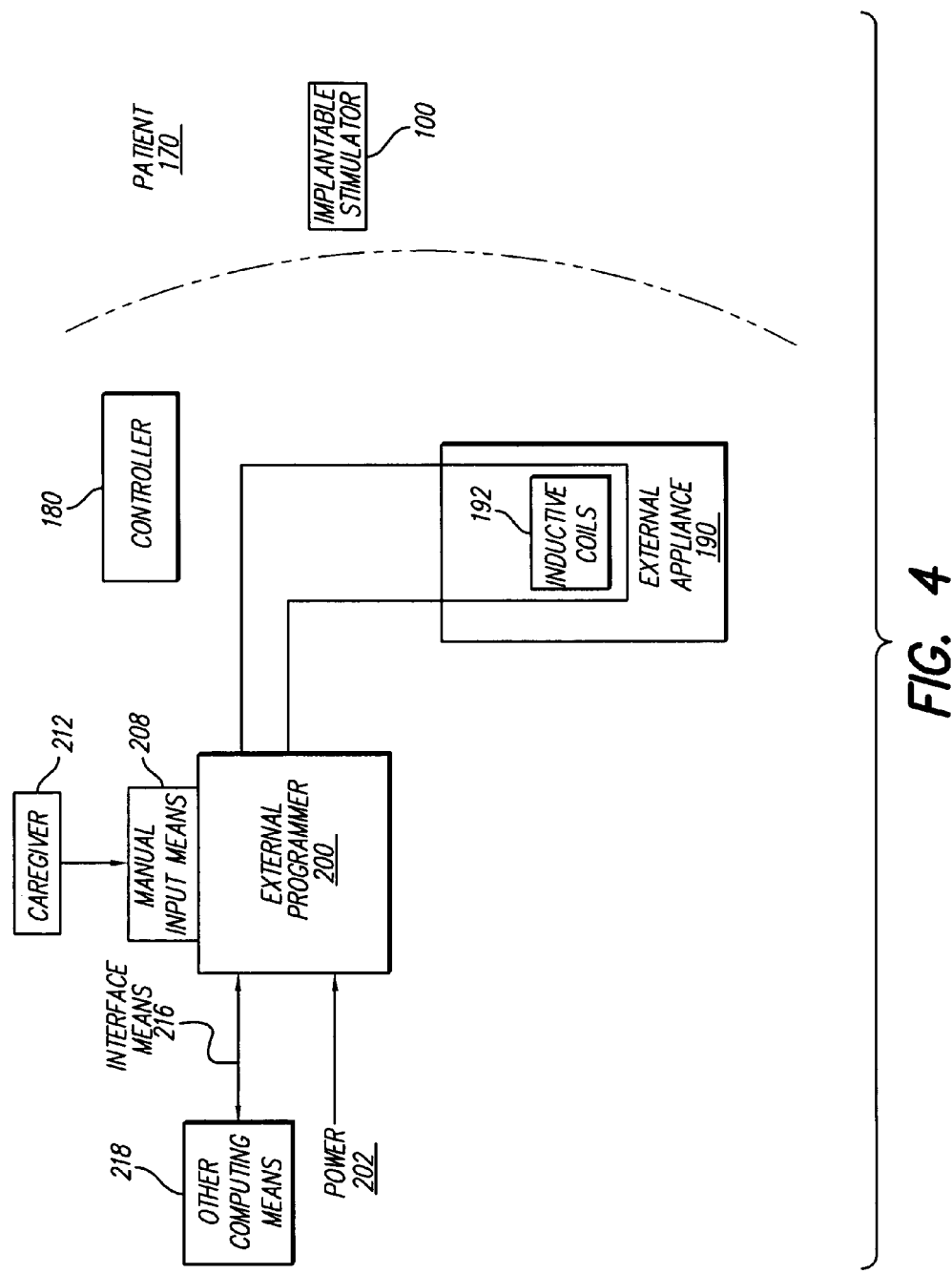
FIG. 4 illustrates possible external components of the invention.

In certain embodiments, and as illustrated in FIG. 4, the patient 170 switches microstimulator 100 on and off by use of controller 180, which may be hand held. Microstimulator 100 is operated by controller 180 by any of various means, including sensing the proximity of a permanent magnet located in controller 180, sensing RF transmissions from controller 180, or the like.

External components for programming and/or providing power to various embodiments of microstimulator 100 are also illustrated in FIG. 4. When communication with microstimulator 100 is desired, patient 170 is positioned on or near external communications appliance 190, which appliance contains one or more inductive coils 192 or other means of communication (e.g., RF transmitter and receiver). External communications appliance 190 is connected to or is a part of external programmer 200 which may receive power 202 from a conventional power source. External programmer 200 contains manual input means 208, e.g., a keypad, whereby the patient 170 or a caregiver 212 can request changes in the stimulation parameters produced during the normal operation of microstimulator 100. In these embodiments, manual input means 208 includes various electromechanical switches and/or visual display devices or the like that provide the patient and/or caregiver with information about the status and prior programming of microstimulator 100.

Alternatively or additionally, external programmer 200 is provided with an interface means 216 for interacting with other computing means 218, such as by a serial interface cable or infrared link to a personal computer or to a telephone modem or the like. Such interface means 216 may permit a clinician to monitor the status of the implant and prescribe new stimulation parameters from a remote location.

The external appliance(s) may be embedded in a cushion, pillow, mattress cover, or garment. Other possibilities exist, including a belt, scarf, patch, or other structure(s) that may be affixed to the patient's body or clothing. External appliances may include a package that can be, e.g., worn on the belt, may include an extension to a transmission coil affixed, e.g., with a VELCRO band or adhesive, or may be combinations of these or other structures able to perform the functions described herein.

In order to help determine the strength and/or duration of electrical stimulation required to produce the desired effect, in some embodiments, a patient's response to and/or need for treatment is sensed. For example, muscle activity (e.g., limb EMG), electrical activity of a nerve (e.g., ENG), and/or electrical activity of the brain (e.g., EEG) may be sensed. Other measures of the state of the patient may additionally or alternatively be sensed. For instance, medication, neurotransmitter, hormone, interleukin, cytokine, lymphokine, chemokine, growth factor, and/or enzyme levels or their changes, and/or levels or changes in other substance(s) borne in the blood and/or in the cerebrospinal fluid (CSF) may be sensed, using, e.g., one or more Chemically Sensitive Field-Effect Transistors (CHEMFETs) such as Enzyme-Selective Field-Effect Transistors (ENFETs) or Ion-Sensitive Field-Effect Transistors (ISFETs, as are available from Sentron CMT of Enschede, The Netherlands). For instance, the level or changes in level of neuron-specific enolase, a key glycolytic enzyme, in either or both the blood serum or CSF may be sensed. As another example, to sense erectile dysfunction, a penile tumescence sensor, penile arteriole pressure sensor, and/or nitric oxide sensor may be used.

As another example, when electrodes of implantable stimulator 100 are implanted on or near the vagus nerve, a sensor or stimulating electrode (or other electrode) of microstimulator 100 may be used to sense changes in EEG resulting from the stimulation applied to the nerve. Alternatively, a "microstimulator" dedicated to sensory processes communicates with a microstimulator that provides the stimulation, pulses. The implant circuitry 104 may, if necessary, amplify and transmit these sensed signals, which may be analog or digital. Other methods of determining the required stimulation include sensing impedance, pressure, acceleration, mechanical stress, and capacitance, as well as other methods mentioned herein, and yet others that will be evident to those of skill in the art upon review of the present disclosure. The sensed information may be used to control stimulation parameters in a closed-loop manner.

As mentioned earlier, use of, for instance, a multi-electrode cuff, where electrodes are present on the inner surface of the cuff, may be used to create UPAPs. In this example of sensing a physical condition of a patient, sense amplifiers may be employed to sense the propagating action potentials that result from the cathodic stimulus from the cuff's stimulating electrode. For instance, a technique (such as described herein) to implement the UPAP is employed, and the signal at each end of the cuff, or at a more remote location(s) on the nerve, is measured. If the UPAP generation is successful, then an action potential will be sensed traveling only in the desired direction, for instance, at only one end of the cuff.

If the UPAP technique is unsuccessful, it may be because (1) no action potential was generated by the stimulus, (2) bi-directional action potentials were generated, (3) a UPAP was generated in the wrong direction. In the case of such a failure, an algorithm can be employed to generate the correct UPAP. For instance, if no action potentials were produced, the cathodic stimulus may be increased until bi-directional action potentials are generated. If bi-directional action potentials were produced or a UPAP was generated in the wrong direction, one of the techniques discussed herein for creating UPAPs may be implemented and adjusted until the UPAP in the appropriate direction results. When using virtual and real electrodes, the configuration and/or stimulus strengths may be adjusted to create the effect. Or, if stimulus waveform characteristics are employed (trapezoidal pulses with an exponential trailing edge), the parameters of the waveforms may be adjusted until the proper UPAPs are generated.

In some instances, the time(s) of arrival of the sensed action potentials and/or evoked potentials at the electrodes may be used to adjust the UPAP-generating mechanisms. Since various nerve fiber types have different conduction velocities, the arrival time of an action potential (as defined by a waveform morphological feature, such as an upstroke, maximum rate of change of sensed amplitude, peak value, zero crossing, or the like) at an electrode some distance from the stimulation site may be used to determine if the UPAP generation was successful, i.e., whether the fiber type to be inhibited is no longer generating action potentials in the direction to be blocked.

In certain instances, the morphology of the sensed action potentials and/or evoked potentials may be used to determine the effectiveness of UPAP generation. At an electrode close to the stimulating electrode, the difference in propagation velocity between fibers is often not great enough to create differences in arrival times between sensed propagating action potentials; that is, the sensed signal at a nearby electrode will be a spatial- and time-averaged waveform that is made up of the traveling action potentials of different fiber types. Techniques for decomposing the waveform into the constituent action potentials from the different fiber types have been proposed. (See, for instance, Barker, et al., "Determination of the Distribution of Conduction Velocities in Human Nerve Trunks" *Biomedical Engineering* 26(2): 76–81, 1979 and Schoonhoven, et al., "The Inverse Problem in Electroneurography-I: Conceptual Basis and Mathematical Formulation" *Biomedical Engineering* 35(10):769–777, 1988.) An algorithm incorporating waveform analysis can be utilized to decompose the sensed signal to determine if the UPAP is successfully arresting the propagation of an action potential from a specific fiber type(s).

As an example, the sensed waveform may be characterized during a calibration routine. A sensed signal may be obtained from the desired UPAP configuration/parameters and compared to a sensed signal obtained from bi-directional propagation configuration/parameters. The state of bi-directional versus unidirectional propagation may be verified by either or both sensed signals and/or by clinical symptoms. The differences in the unidirectional and bi-directional waveforms could be characterized by a feature or suite of features indicating the differences.

For instance, if it is reliably determined that the peak value of the sensed action potential from a fiber is related to the square of the conduction velocity of that fiber, then, given a known or assumed distribution of fibers within the cuff electrode, the fibers which are propagating action potentials may be inferred from the amplitude of the compound action potential (CAP) waveshape. As an example, if larger fibers (which have higher conduction velocities) are to be blocked by UPAP techniques, then, during bidirectional propagation (e.g., for calibration), large sensed CAP waveforms would be detected on the electrode in the direction to be blocked. When the UPAP technique is successful, a dramatic reduction in sensed signal amplitude will result, due to blocked propagation of the larger fibers. There may still be a propagated CAP of lower amplitude sensed by the electrode due to some smaller fibers being activated by the cathodic stimulus, but a sense threshold can be established, where signals that exceed this threshold indicate propagation by larger fibers and failure of the UPAP method.

In an alternative example, if sense electrodes are placed at each end of a nerve cuff, a differential comparison can be made. After timing and gain adjustments are made, a large difference in signal amplitude between the two electrodes would indicate UPAP success, where a small difference in signals would indicate either loss of nerve capture or bilateral propagation.

Again, the stimulator may sense a physical condition of a patient by monitoring the sensed signal(s) for the characteristic feature(s) to determine if the UPAP generation was successful. If the UPAP succeeded, no changes need be made to the stimulator parameters or configuration. If the UPAP failed, stimulator parameter(s) and/or configuration may be modified until the desired UPAP is recreated, as indicated by the sensed, characteristic waveform that indicates the UPAP. This system may be periodically recalibrated, either automatically or during follow-up sessions with a clinician.

While a microstimulator may also incorporate means of sensing one or more conditions of the patient, it may alternatively or additionally be desirable to use a separate or specialized implantable device to sense and telemeter physiological conditions/responses in order to adjust stimulation parameters. This information may be transmitted to an external device, such as external appliance 190, or may be transmitted directly to implanted stimulator(s) 100. However, in some cases, it may not be necessary or desired to include a sensing function or device, in which case stimulation parameters are fixed and/or determined and refined, for instance, by patient feedback, or the like.

Thus, it is seen that in accordance with the present invention, one or more external appliances may be provided to interact with microstimulator 100, and may be used to accomplish, potentially among other things, one or more of the following functions:

Function 1: If necessary, transmit electrical power from external programmer 200 via appliance 190 to microstimulator 100 in order to power the device and/or recharge power source/storage device 126. External programmer 200 may include an algorithm that adjusts stimulation parameters automatically whenever microstimulator(s) 100 is/are recharged, whenever communication is established between them, and/or when instructed to do so.

Function 2: Transmit data from external programmer 200 via external appliance 190 to implantable stimulator 100 in order to change the operational parameters (e.g., electrical stimulation parameters) used by stimulator 100.

Function 3: Transmit sensed data indicating a need for treatment or in response to stimulation from neurostimulator 100 (e.g., EEG, change in neurotransmitter or medication level, or other activity) to external programmer 200 via external appliance 190.

Function 4: Transmit data indicating state, address and/or type of implantable stimulator 100 (e.g., battery level, stimulation settings, etc.) to external programmer 200 via external appliance 190.

For the treatment of various types and degrees of medical conditions, it may be desirable to modify or adjust the algorithmic functions performed by the implanted and/or external components, as well as the surgical approaches, in ways that would be obvious to skilled practitioners of these arts. For example, in some situations, it may be desirable to employ more than one implantable stimulator 100, each of which could be separately controlled by means of a digital address. Multiple channels and/or multiple patterns of stimulation might thereby be programmed by the clinician and controlled by the patient in order to, for instance, stimulate larger areas of neural tissue in order to maximize therapeutic efficacy.

In some embodiments discussed earlier, microstimulator 100, or a group of two or more microstimulators, is controlled via closed-loop operation. A need for and/or response to stimulation is sensed via microstimulator 100, or by an additional microstimulator (which may or may not be dedicated to the sensing function), or by another implanted or external device. If necessary, the sensed information is transmitted to microstimulator 100. In some embodiments, the stimulation parameters used by microstimulator 100 are automatically adjusted based on the sensed information. Thus, the stimulation parameters are adjusted in a closed-loop manner to provide stimulation tailored to the need for and/or response to stimulation.

For instance, in some embodiments of the present invention, a first and second "stimulator" are provided. The second "stimulator" periodically (e.g. once per minute) records e.g., nerve activity (or medication, etc.), which it transmits to the first stimulator. The first stimulator uses the sensed information to adjust stimulation parameters according to an algorithm programmed, e.g., by a clinician. For example, stimulation may be activated (or stimulation current amplitude may be increased) in response to EEG changes indicative of an impending or an actual seizure. As another example, when the microstimulator is used to stimulate the cavernous nerve to produce an erection, stimulation current amplitude may be increased in response to a decrease in intracavernosal pressure. Alternatively, one "microstimulator" performs both the sensing and stimulating functions.

Figure 5:
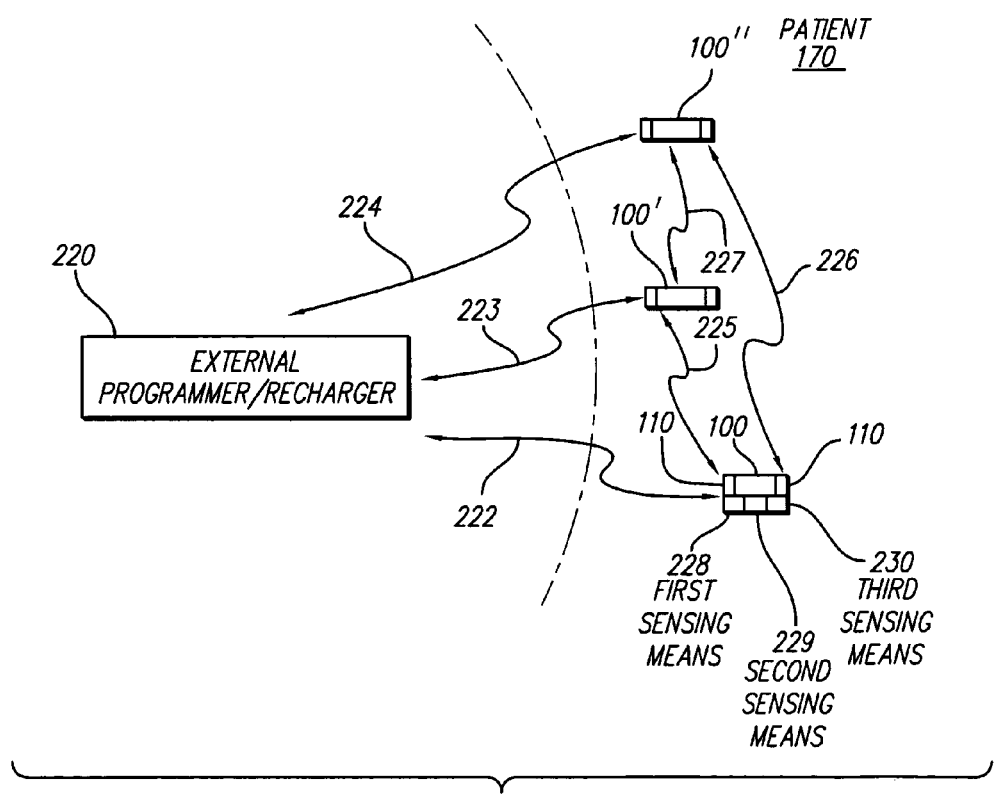
FIG. 5 depicts a system of implantable devices that communicate with each other and/or with external control/programming devices.

For example, as shown in the example of FIG. 5, a first microstimulator 100, implanted beneath the skin of patient 170, provides electrical stimulation via electrodes 110 to a first location; a second microstimulator 100' provides electrical stimulation to a second location; and a third microstimulator 100" provides electrical stimulation to a third location. As mentioned earlier, the implanted devices may operate independently or may operate in a coordinated manner with other similar implanted devices, other implanted devices, or other devices external to the patient's body, as shown by the control lines 222, 223 and 224 in FIG. 5. That is, in accordance with certain embodiments of the invention, external controller 220 controls the operation of each of the implanted microstimulators 100, 100' and 100". According to various embodiments of the invention, an implanted device, e.g. microstimulator 100, may control or operate under the control of another implanted device(s), e.g., microstimulator 100' and/or microstimulator 100". That is, a device made in accordance with the invention may communicate with other implanted stimulators, other implanted devices, and/or devices external to a patient's body, e.g., via an RF link, an ultrasonic link, a thermal link, an optical link, or other communications link. Specifically, as illustrated in FIG. 5, microstimulator 100, 100', and/or 100", made in accordance with the invention, may communicate with an external remote control (e.g., patient and/or physician programmer 220) that is capable of sending commands and/or data to implanted devices and that may also be capable of receiving commands and/or data from implanted devices.

For instance, two or more stimulators may be used in a UPAP system. One stimulator may depolarize the nerve, inducing bi-directional propagation of action potentials. One or more additional stimulators may be responsible for hyperpolarizing the nerve, or certain fiber types within the nerve. The stimulators may communicate with each other to coordinate these activities, or they may communicate with and/or receive communications from an external controller. The stimulation parameters and/or timing may be fixed, adjusted manually, and/or automatically updated based on sensed physical condition(s) of the patient. One or more microstimulators included in the system may include a fixation device, such as a nerve cuff. For instance, in certain embodiments, the stimulator(s) used for hyperpolarizing include a nerve cuff, while the stimulator(s) for depolarizing do not.

A microstimulator made in accordance with the invention may incorporate, in some embodiments, first sensing means 228 for sensing therapeutic effects, clinical variables, or other indicators of the state of the patient, such as EEG, ENG, and/or EMG. The stimulator additionally or alternatively incorporates second means 229 for sensing levels or changes in one or more medications, neurotransmitters, hormones, interleukins, cytokines, lymphokines, chemokines, growth factors, enzymes, and/or other substances in the blood plasma, in the cerebrospinal fluid, or in the local interstitial fluid. The stimulator additionally or alternatively incorporates third means 230 for sensing electrical current levels and/or waveforms. Sensed information may be used to control the parameters of the stimulator(s) in a closed loop manner, as shown by control lines 225, 226, and 227. Thus, the sensing means may be incorporated into a device that also includes electrical stimulation means, or the sensing means (that may or may not have stimulating means) may communicate the sensed information to another device(s) with stimulating means, or to another device capable of commanding other devices to stimulate. For instance, a "central" device can analyze the sensed data and command other devices to stimulate appropriately. This central device may or may not be implanted.

As described earlier, the present invention teaches a microstimulator system for stimulation of a nerve with unidirectionally propagating action potentials that may effectively select the efferent fibers or the afferent fibers propagating more towards the periphery and viscera or more towards the CNS. Such selective stimulation may be an effective treatment for a variety of disorders. For instance, and as discussed in more detail below, stimulation of the vagus nerve with unidirectionally propagating action potentials that effectively select and stimulate the therapeutic afferent fibers of the vagus nerve may be an effective treatment for a variety of disorders, including epilepsy and/or depression.

A commercially available vagus nerve stimulation (VNS) system is currently used as a therapy for refractory epilepsy. Epilepsy afflicts one to two percent of the population in the developed world, and an estimated 25–33% of these are refractory to medication and conventional surgery. The currently available VNS system produces a significant number of side effects due to recruitment of efferent fibers.

Figure 6A:
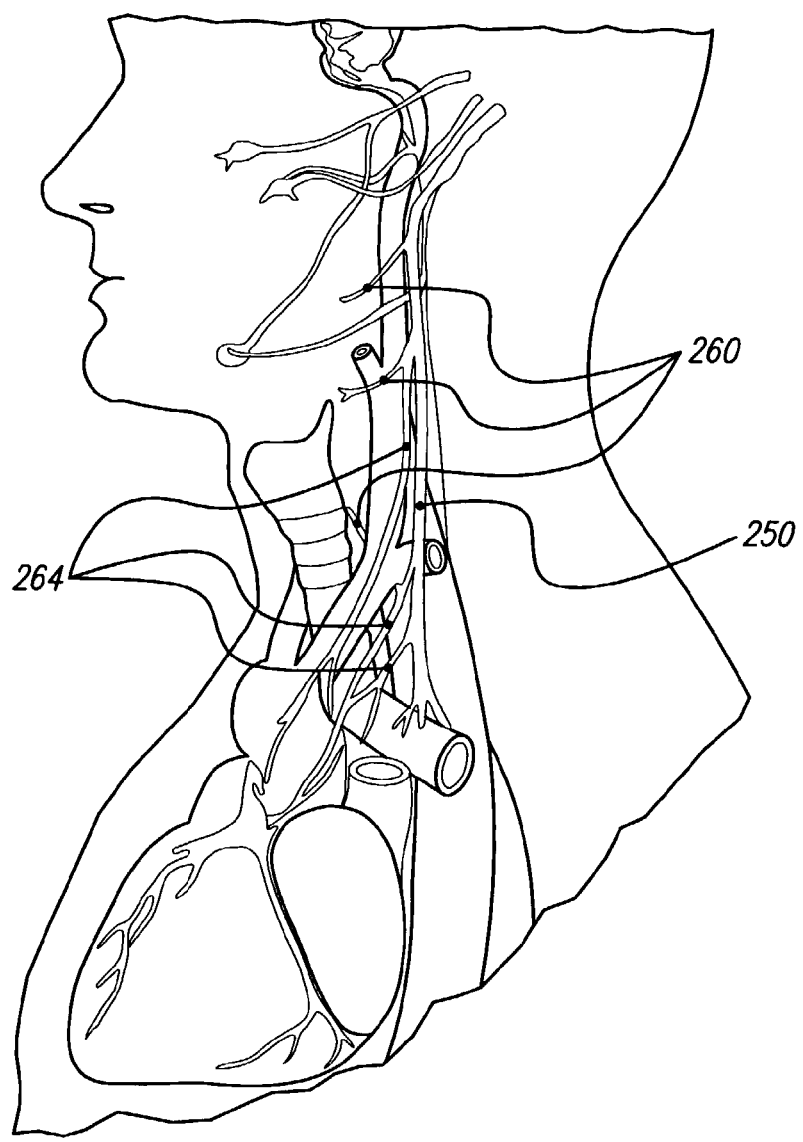
FIG. 6A illustrates various autonomic nerves in the head, neck, and thorax.
Figure 6B:
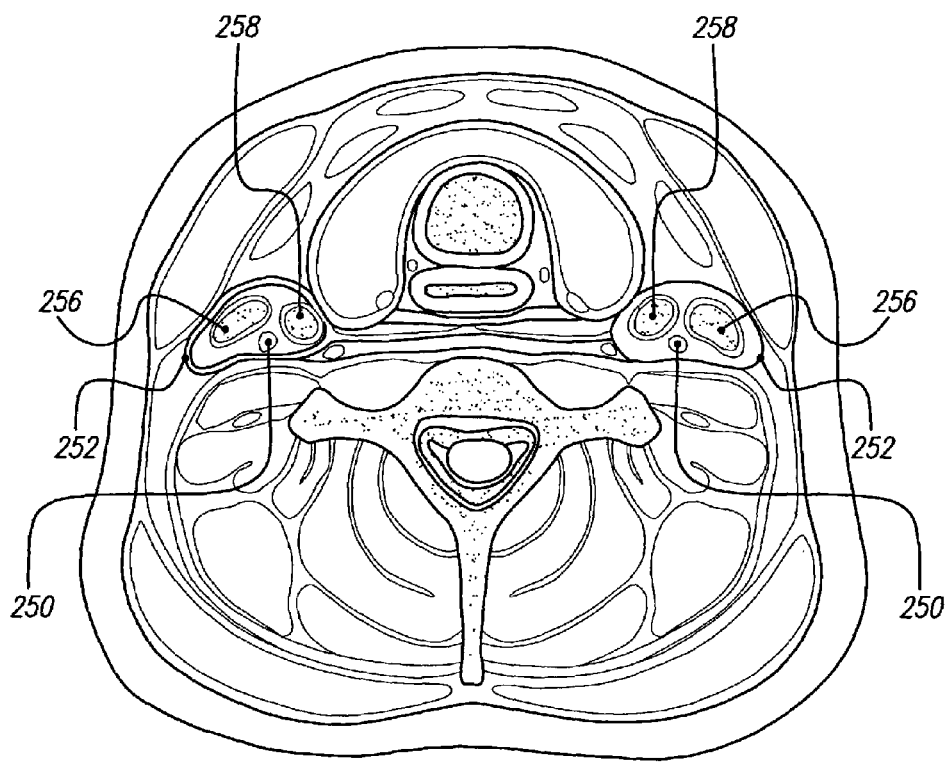
FIG. 6B is a cross-section through the neck, at the level of cervical vertebra C7.
Figure 6C:
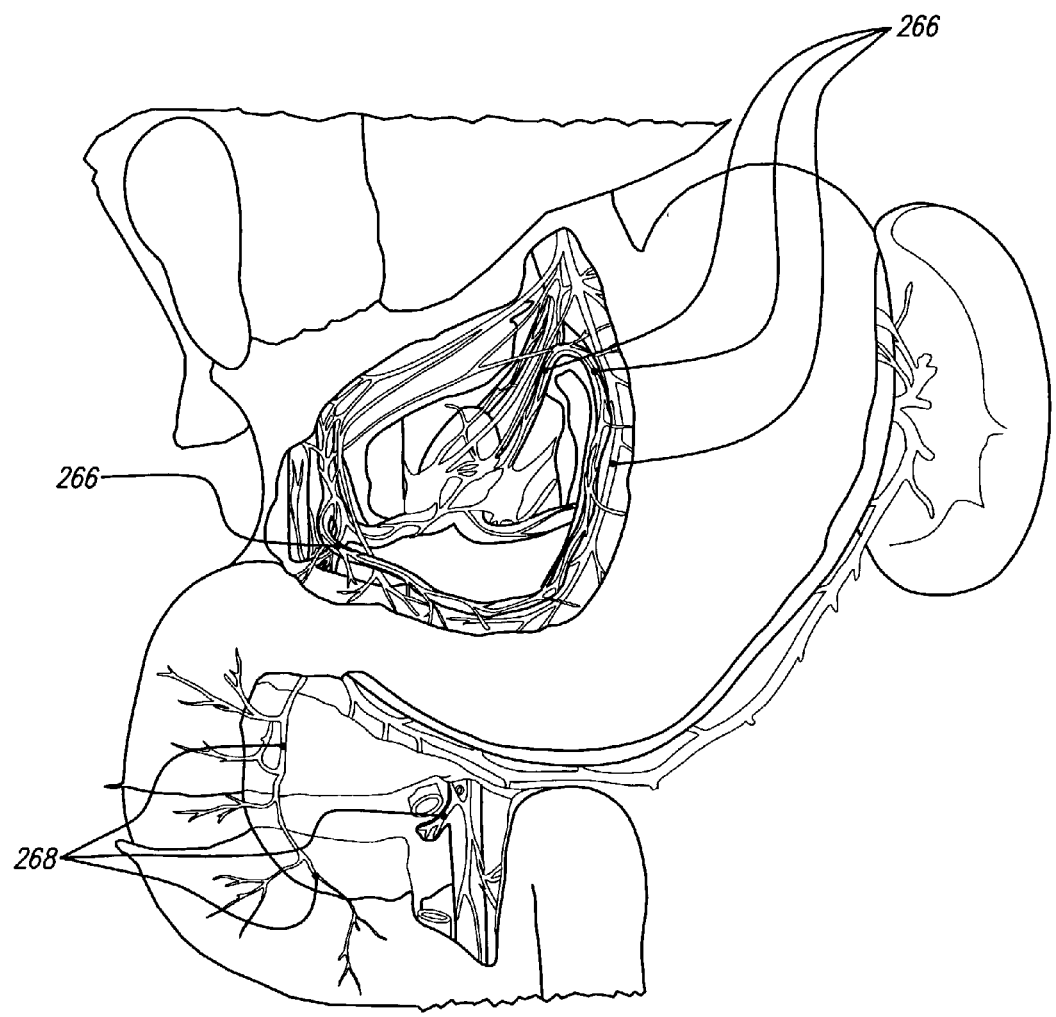
FIG. 6C illustrates various autonomic nerves in the abdomen.
Figure 7A:
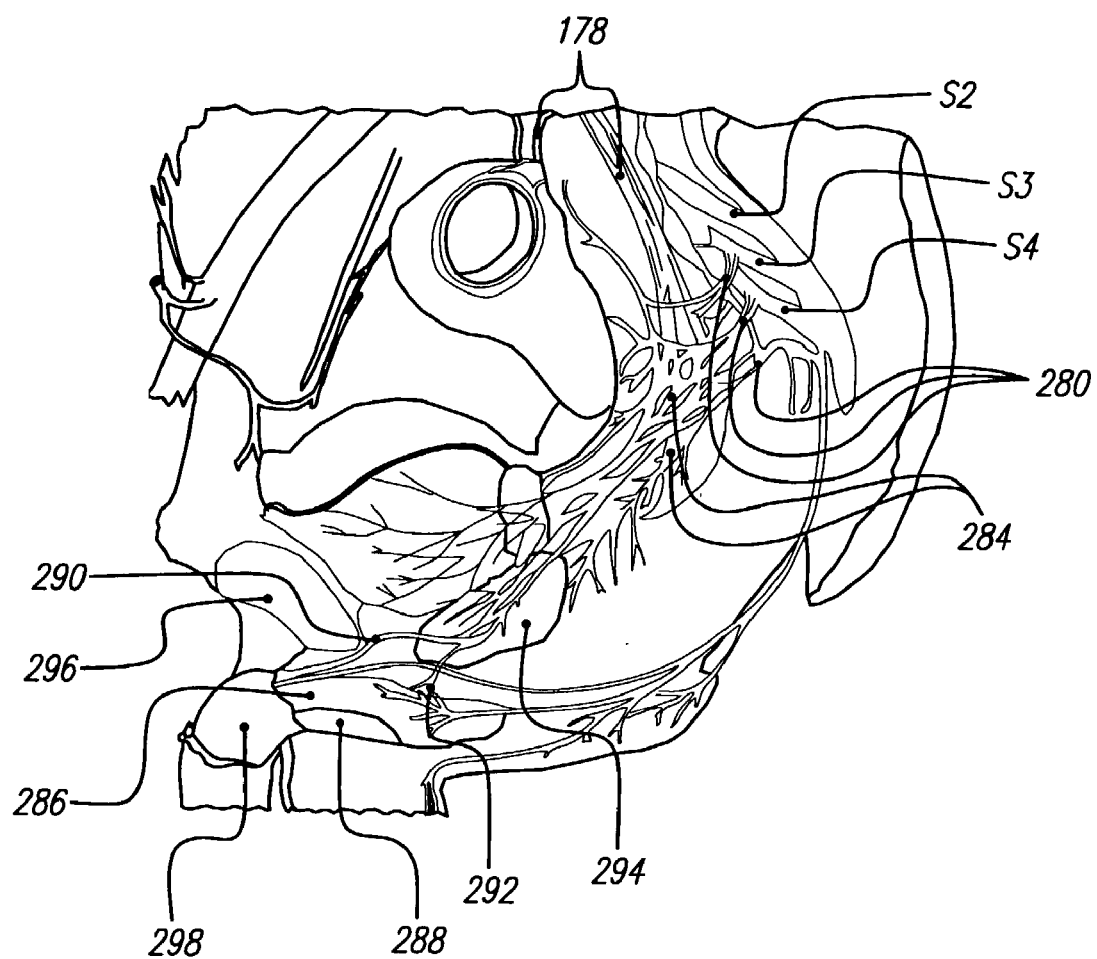
FIG. 7A depicts the nerves of the male pelvic viscera and surrounding anatomy, where a stimulation system of the present invention may be implanted.
Figure 7B:
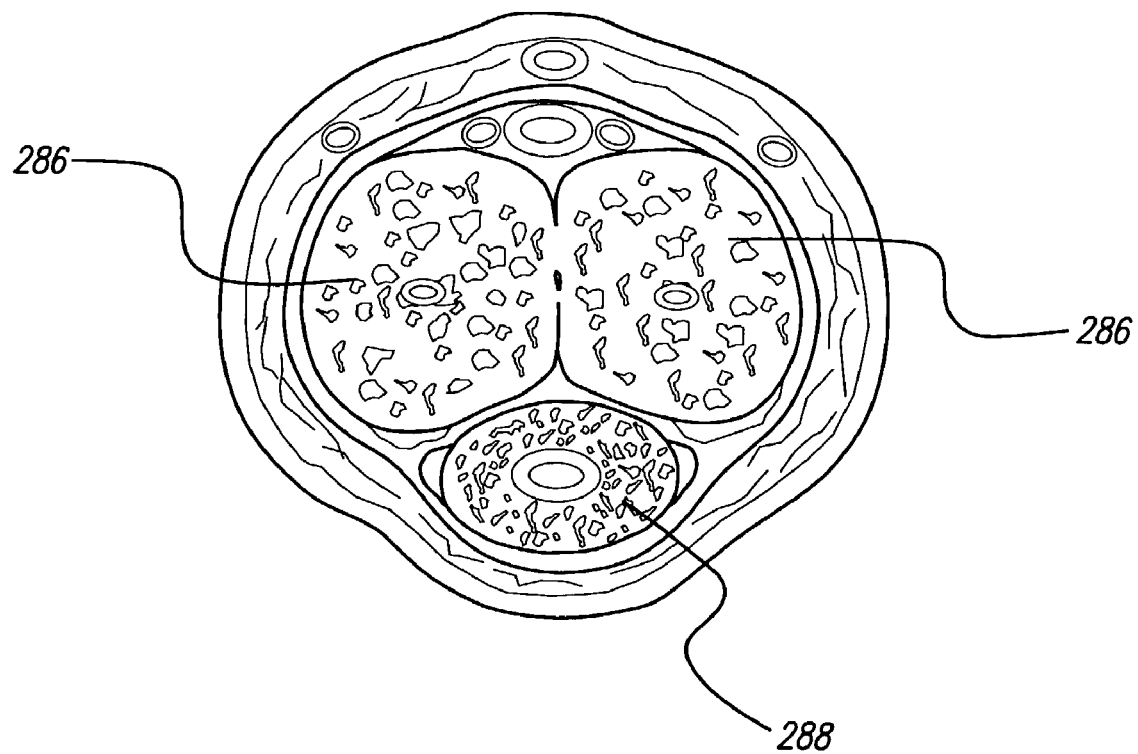
FIG. 7B is a section view through the body of a penis.

The vagus nerve 250 (see FIGS. 6A, 6B, and 6C) provides the primary parasympathetic nerve to the thoracic organs and most of the abdominal organs. It originates in the brainstem and runs in the neck through the carotid sheath 252 (FIG. 6B) with jugular vein 256 and common carotid artery 258, and then adjacent to the esophagus to the thoracic and abdominal viscera. As seen in FIGS. 6A and 6C, vagus nerve 250 has many branches, including pharyngeal and laryngeal branches 260, cardiac branches 264, gastric branches 266, and pancreaticoduodenal branches 268. Because the vagus nerve innervates the pharynx, the most common side effect associated with VNS therapy is a hoarse voice during stimulation. Some patients also experience a mild cough, tickling in the back of the pharynx, or increased hoarseness. Stimulation of the vagus nerve may also lead to a decreased opening of the vocal cords, which results in shortness of breath during exertion.

The vagus nerve provides parasympathetic innervation to the heart, and stimulation of the vagus nerve has been demonstrated to cause bradycardia and arrhythmias. Stimulation of the left vagus nerve distal to the cardiac branch of the vagus nerve has not resulted in significantly increased cardiac side effects; however, the stimulating electrodes may only be safely placed on this distal portion of the left vagus nerve. Bilateral stimulation is not allowed, as stimulation of the right vagus nerve produces significant cardiac side effects. Finally, the vagus nerve provides parasympathetic innervation to the lungs and most of the abdominal organs (e.g., the stomach and small intestine), and improper stimulation of the vagus nerve may impair proper functioning of these organs.

Some embodiments of this invention include a microstimulator that generates UPAPs of the vagus nerve (which, as used herein, includes branches of the vagus nerve). A microstimulator may be implanted on or near the vagus nerve in the neck region, e.g., by dissecting down to the carotid sheath. A microstimulator may also/instead be surgically implanted on or near a more proximal or distal portion of the vagus nerve. Various stimulator configurations may be used. For instance, a cuff electrode, which may be part of a microstimulator, attached to a microstimulator via a short lead, or attached to an IPG, may be implanted around the vagus nerve.

A single microstimulator may be implanted, or two or more microstimulators may be implanted to achieve greater stimulation of the vagus nerve. According to some embodiments of the invention, a single microstimulator is implanted for stimulation of the left vagus nerve. According to various embodiments of the invention, one microstimulator is implanted for stimulation of the left vagus nerve and another is implanted for stimulation of the right vagus nerve. Bilateral stimulation may be effected with two separate microstimulators or by a microstimulator with multiple leads. Vagus nerve stimulation with UPAPs may alternatively or additionally be provided by one or more IPGs attached to one or more leads with, for instance, electrodes in a nerve cuff.

For instance, a UPAP system (e.g., a microstimulator with a fixation device, a nerve cuff attached to an IPG implanted in a subclavicular location, or the like) may be provided on the vagus nerve in the carotid sheath (unilaterally or bilaterally). Stimulation parameters may comprise, for instance, a stimulation pulse with a quasitrapezoidal shape, with a plateau pulse width in the range of about 10 μsec to about 5 msec and/or an exponentially decaying trailing phase having a fall time in the range of about 50 μsec to about 5 msec. A charge recovery pulse, may comprise, for instance, a quasitrapezoidal shape with a plateau pulsewidth of about 50 μsec to about 10 msec and/or a decaying trailing phase with a fall time of about 50 μsec to about 5 msec. Other possible UPAP parameters are taught herein. In some electrode configurations, for instance tripolar or other multipolar configurations, means for distributing the current asymmetrically between the electrodes may be included, i.e., the polarities and currents of the electrodes are independently programmable.

According to such an embodiment of the invention, the stimulation can increase excitement of afferent fibers of the vagus nerve(s), thereby treating epilepsy and/or depression, while limiting side effects typically caused by bidirectional stimulation that activates efferent fibers with orthodromically propagating action potentials. Low-frequency electrical stimulation (i.e., less than about 50–100 Hz) is likely to produce the therapeutic activation. To determine the need for and/or response to such treatment, EEG of the cortex, thalamus, a region adjacent to a scarred region of the brain, or any area of the brain known to give rise to a seizure in a particular patient, may be sensed. Alternatively or additionally, limb EMG and/or other conditions, as known to those of skill in the art, may be sensed.

Additional uses include the application to tachycardia via effective selection and stimulation of the efferent fibers of the vagus nerve, such as one or more superior and/or inferior cardiac branches. Electrodes capable of UPAP may be provided on the right and/or left vagus nerve(s) in, for instance, the neck, the thorax, and/or adjacent to the esophagus. Excitatory stimulation (i.e., less than about 50–100 Hz) should be used to stimulate vagal parasympathetic activity to the heart to promote a decrease in heart rate and thereby treat tachycardia. To determine the need for and/or response to such treatment, ECG, heart rate, blood pressure, blood flow, cardiac output, acceleration, and/or breathing, for instance, may be sensed.

As another example, stimulation of the cavernous nerve(s) with unidirectionally propagating action potentials that effectively select the therapeutic parasympathetic efferent fibers of the cavernous nerve(s) may be an effective treatment for erectile dysfunction and may minimize distracting, unpleasant, or uncomfortable sensation that may be associated with electrical stimulation of the cavernous nerve(s).

Recent estimates suggest that the number of men in the U.S. with erectile dysfunction may be 10–20 million, and inclusion of men with partial erectile dysfunction increases the estimate to about 30 million. Erectile dysfunction has a number of causes, both physiological and psychological, and in many patients the disorder is multifactorial. The causes include several that are essentially neurologic in origin. Damage to the autonomic pathways innervating the penis may eliminate "psychogenic" erection initiated by the central nervous system. Lesions of the somatic nervous pathways may impair reflexogenic erections and may interrupt tactile sensation needed to maintain psychogenic erections. Spinal cord lesions may produce varying degrees of erectile failure depending on the location and completeness of the lesions. Not only do traumatic lesions affect erectile ability, but disorders leading to peripheral neuropathy may impair neuronal innervation of the penis or of the sensory afferents.

A well-publicized medication is available for erectile dysfunction, but it requires an hour to exert its full effects, and it may have significant side effects such as abnormal vision, flushing, headache, and diarrhea. Intracavernosal injection therapy, in which a patient injects vasodilator substances (e.g., papaverine) into the corpora of the penis, suffers a high rate of patient dropout, as do vacuum constriction devices. Several forms of penile prostheses are available, including semirigid, malleable, and inflatable, but these have significant problems with mechanical failure, infection, and erosions.

The male erectile response is a vascular event initiated by neuronal action and maintained by a complex interplay between vascular and neurological events. The pelvic splanchnic nerve plexus 280, the nerve fibers of which originate in the sacral spinal cord (S2, S3, S4, respectively) and intertwine with the inferior hypogastric plexus 284, provides the primary parasympathetic input to the penis, i.e., the corpus cavernosa 286 and the corpus spongiosum 288, via the greater cavernous nerve 290 and lesser cavernous nerve 292. This parasympathetic input allows erection by relaxation of the smooth muscle and dilation of the helicine arteries of the penis. The cavernous nerves 290, 292 pass bilaterally near the apex, mid, and base of prostate 294 and then near the posterolateral urethra (not shown). The nerves then run underneath the pubic symphysis 296 and into the penis. Conversely, sympathetic innervation from the hypogastric nerves, specifically from the inferior hypogastric plexus 284, makes the penis flaccid due to constriction of the smooth muscle and helicine arteries of the penis.

One or more stimulators may be implanted to stimulate cavernous nerve(s) 290, 292, branches thereof, and/or nerves that give rise to a cavernous nerve(s) (collectively referred to herein simply as cavernous nerves) in any of the aforementioned regions by dissecting down to the nerve(s). Such dissection may usually be performed through any incision allowing access to the prostate and/or the posterolateral urethra. For example, an incision could be made above the pubic symphysis 296, and the tissues between the incision and at least one of the cavernous nerves could be dissected away. Alternatively, an incision may be made immediately below the pubic symphysis 296, or an incision may be made through the perineum. As another alternative, an incision may be made in the dorsolateral penis 298.

Some embodiments of this invention include a stimulator that allows UPAPs of the cavernous nerve(s). Such a stimulator (for instance, a microstimulator of the present invention) allows the effective selection of efferent fibers. Via stimulation of primarily efferent fibers, unidirectional stimulation of the cavernous nerve(s) may be an effective treatment for erectile dysfunction. By effectively avoiding the production of orthodromic action potentials on the afferent fibers, such stimulation may minimize distracting, unpleasant, or uncomfortable sensation that may be associated with electrical stimulation of the cavernous nerve(s) or other associated nerve fibers, as mentioned above.

According to such an embodiment of the invention, a UPAP system (e.g., a microstimulator with a fixation device or a nerve cuff attached to an IPG implanted in the abdomen or the like) may be provided on one or more cavernous nerves or neurovascular bundles containing a cavernous nerve. Stimulation parameters may comprise, for instance, a stimulation pulse with a quasitrapezoidal shape, with a plateau pulse width in the range of about 10 μsec to about 5 msec and an exponentially decaying trailing phase having a fall time in the range of about 50 μsec to about 5 msec. A charge recovery pulse, may comprise, for instance, a quasitrapezoidal shape with a plateau pulsewidth of about 50 μsec to about 10 msec and a decaying trailing phase with a fall time of about 50 μsec to about 5 msec. Again, other possible UPAP parameters are taught herein. In some electrode configurations, for instance, tripolar or other multipolar configurations, means for distributing the current asymmetrically between the electrodes may be included, i.e., the polarities and currents of the electrodes are independently programmable.

The stimulation can increase excitement of a nerve(s), such as a cavernous nerve(s), thereby treating erectile dysfunction. Low-frequency electrical stimulation (i.e., less than about 50–100 Hz) is likely to produce such activation. To determine the need for and/or response to such treatment, a penile tumescence sensor, penile arteriole pressure sensor, and/or nitric oxide sensor, for instance, may be used.

A single microstimulator may be implanted, or two or more systems may be implanted to achieve greater stimulation of a cavernous nerve(s). According to one embodiment of the invention, a single microstimulator is implanted for stimulation of a single cavernous nerve. According to another embodiment of the invention, one microstimulator is implanted for stimulation of one of the left cavernous nerves and another is implanted for stimulation of one of the right cavernous nerves. According to other embodiments, several microstimulators are used: one for each nerve to be stimulated, or even multiple for each nerve to be stimulated. Bilateral stimulation and other multiple stimulation site treatments may be effected with two separate microstimulators or by a microstimulator with multiple leads. Cavernous nerve stimulation with UPAPs may alternatively or additionally be provided by one or more IPGs attached to one or more leads with, for instance, electrodes in a nerve cuff.

Additionally, sensing means described earlier may be used to orchestrate first the activation of microstimulator(s)/electrode(s) targeting one area of a nerve, and then, when appropriate, the microstimulator(s)/electrode(s) targeting the same or another area of the nerve, in order to, for instance, implement UPAPs. Alternatively, this orchestration may be programmed, and not based on a sensed condition.

While the invention herein disclosed has been described by means of specific embodiments and applications thereof, numerous modifications and variations could be made thereto by those skilled in the art without departing from the scope of the invention set forth in the claims.

What is claimed is:

1. Method of stimulating a cavernous nerve, the method comprising:
    providing at least one implantable stimulator with at least two electrodes;
    disposing the electrodes to independently apply stimulation that unidirectionally propagates action potentials along one of the left cavernous nerve and the right cavernous nerve; and
    applying the stimulation to generate unidirectionally propagating action potentials in efferent fibers in one of the left cavernous nerve and the right cavernous nerve, thereby treating erectile dysfunction while limiting side effects of bidirectional stimulation.

2. The method of claim 1 wherein providing at least one implantable stimulator comprises providing at least one microstimulator.

3. The method of claim 1 further comprising applying the stimulation at less than about 50–100 Hz.

4. The method of claim 1 further comprising applying the stimulation with a stimulation pulse with at least one of a plateau pulsewidth of about 10 µsec to about 5 msec and a decaying trailing phase with a fall time of about 50 µsec to about 5 msec and a charge recovery pulse with at least one of a plateau pulsewidth of about 50 µsec to about 10 msec and a decaying trailing phase with a fall time of about 50 µsec to about 5 msec.

5. The method of claim 1 wherein at least one of the electrodes is a virtual electrode.

6. The method of claim 1 wherein the stimulator includes at least three electrodes.

7. The method of claim 6 wherein at least one of the electrodes is a virtual electrode.

8. The method of claim 1 further comprising sensing at least one physical condition of a patient.

9. The method of claim 8 wherein the at least one sensed physical condition includes at least one of penile tumescence, penile arteriole pressure, nitric oxide concentration, and action potentials propagating along the cavernous nerve.

10. The method of claim 8 further comprising determining at least one of a configuration of the electrodes and the stimulation to apply based on the at least one physical condition of the patient.

11. The method of claim 1 wherein the cavernous nerve comprises at least one cavernous nerve, including the left cavernous nerves, the right cavernous nerves, branches of the left cavernous nerves, branches of the right cavernous nerves, nerves that give rise to at least one cavernous nerve, and neurovascular bundles containing at least one cavernous nerve.

12. Method of stimulating a cavernous nerve, the method comprising:
    providing at least one implantable stimulator that includes at least two electrodes;
    implanting the stimulator so that the electrodes are disposed to stimulate one of the left cavernous nerve and the right cavernous nerve independently; and
    applying stimulation to efferent fibers of the one of the left cavernous nerve and the right cavernous nerve thereby treating erectile dysfunction while limiting side effects of bidirectional stimulation.

13. The method of claim 12 wherein providing at least one implantable stimulator comprises providing at least one microstimulator.

14. The method of claim 13 wherein the at least one microstimulator comprises a programmably configurable microstimulator with at least two activated electrodes configured as a first cathode and a first anode.

15. The method of claim 12 wherein the electrodes comprise at least a first cathode and a first anode, and the method further comprises:
    applying a depolarizing cathodic current to a nerve via the first cathode, which cathodic current is sufficient to initiate bidirectional action potentials in large diameter nerve fibers and small diameter nerve fibers;
    applying a hyperpolarizing anodic current to the nerve via the first anode at a side of the cathode where arrest of the action potentials is desired; and
    tapering the anodic current.

16. Method of stimulating a cavernous nerve, the method comprising:
    providing at least one implantable stimulator with at least a first cathode and a first anode;
    implanting the stimulator so that the electrodes are disposed to stimulate one of the left cavernous nerve and the right cavernous nerve independently; and
    applying the stimulation to one of the left cavernous nerve and the right cavernous nerve to generate orthodromic action potentials traveling in one direction along the nerve, including
        applying a depolarizing cathodic current to a nerve via the first cathode, which cathodic current is sufficient to initiate bidirectional action potentials in large diameter nerve fibers and small diameter nerve fibers, applying a hyperpolarizing anodic current to the nerve via the first anode at a side of the cathode where arrest of the action potentials is desired, and tapering the anodic current, thereby limiting side effects of bidirectional stimulation.

17. The method of claim 16 further comprising applying the hyperpolarizing current before the action potentials pass the first anode, which hyperpolarizing current is relatively high-amplitude hyperpolarizing current, which high-amplitude hyperpolarizing current is sufficient to arrest action potentials in large diameter nerve fibers and small diameter nerve fibers.

18. The method of claim 16 further comprising waiting an amount of time allowing the action potentials to propagate in the large diameter nerve fibers, then applying the hyperpolarizing anodic current to the nerve at the side of the cathode where arrest of the action potentials in the small diameter nerve fibers is desired, which hyperpolarizing current arrests action potentials in the small diameter nerve fibers.

19. The method of claim 16 further comprising applying the hyperpolarizing current before the action potentials pass the first anode, which hyperpolarizing current is a relatively low-amplitude hyperpolarizing current, which low-amplitude hyperpolarizing current is sufficient to arrest action potentials in large diameter nerve fibers and allows propagation of action potentials in small diameter nerve fibers.

* * * * *